(12) United States Patent
Fabis

(10) Patent No.: US 9,938,520 B2
(45) Date of Patent: Apr. 10, 2018

(54) PREPARATION OF SILICA PARTICLES

(71) Applicant: QIAGEN GmbH, Hilden (DE)

(72) Inventor: Roland Fabis, Leverkusen (DE)

(73) Assignee: QIAGEN GmbH, Hilden (DE)

( * ) Notice: Subject to any disclaimer, the term of this patent is extended or adjusted under 35 U.S.C. 154(b) by 142 days.

(21) Appl. No.: 14/650,645

(22) PCT Filed: Dec. 11, 2013

(86) PCT No.: PCT/EP2013/076150
§ 371 (c)(1),
(2) Date: Jun. 9, 2015

(87) PCT Pub. No.: WO2014/090838
PCT Pub. Date: Jun. 19, 2014

(65) Prior Publication Data
US 2015/0307870 A1   Oct. 29, 2015

(30) Foreign Application Priority Data

Dec. 11, 2012   (EP) ................................. 12196503

(51) Int. Cl.
*B32B 5/16*   (2006.01)
*C01B 33/113*   (2006.01)
(Continued)

(52) U.S. Cl.
CPC ......... *C12N 15/1013* (2013.01); *C01G 49/06* (2013.01); *C01G 49/08* (2013.01);
(Continued)

(58) Field of Classification Search
CPC ........ C04B 35/62807; C04B 35/62849; C04B 2235/3272; C04B 2235/5436; C04B 2235/5445; C01P 2006/42; C09C 1/24
(Continued)

(56) References Cited

U.S. PATENT DOCUMENTS

| 2,885,366 A | 5/1959 | Iler |
| 3,678,144 A | 7/1972 | Shoup |

(Continued)

FOREIGN PATENT DOCUMENTS

| DE | 10 2006 054 173 A1 | 5/2008 |
| DE | 10 2008 063 001 A1 | 6/2010 |

(Continued)

OTHER PUBLICATIONS

Solberg & Landry, Adsorption of DNA into Mesoporous silica, J. Phys. Chem. B 2006, 110, 15261-15268.*

(Continued)

*Primary Examiner* — Hoa T Le

(74) *Attorney, Agent, or Firm* — Seed IP Law Group LLP

(57) ABSTRACT

The present invention provides a cost-efficient method for producing particles having a $SiO_2$ containing surface wherein said method comprises a) providing an aqueous reaction composition comprising i) core particles, ii) an added base, iii) a silicate salt, and iv) a pH modulator wherein the pH value of the reaction composition is above the gelation pH value; b) agitating said reaction composition, wherein the pH modulator decreases the pH value of the reaction composition over time and wherein due to said decrease of the pH value of the reaction composition $SiO_2$ is deposited onto the core particles, whereby particles are formed which have a diameter of 30 µm or less; and c) obtaining the particles. Furthermore, silica particles having high nucleic acid binding properties are provided.

35 Claims, 4 Drawing Sheets

Figure 1:
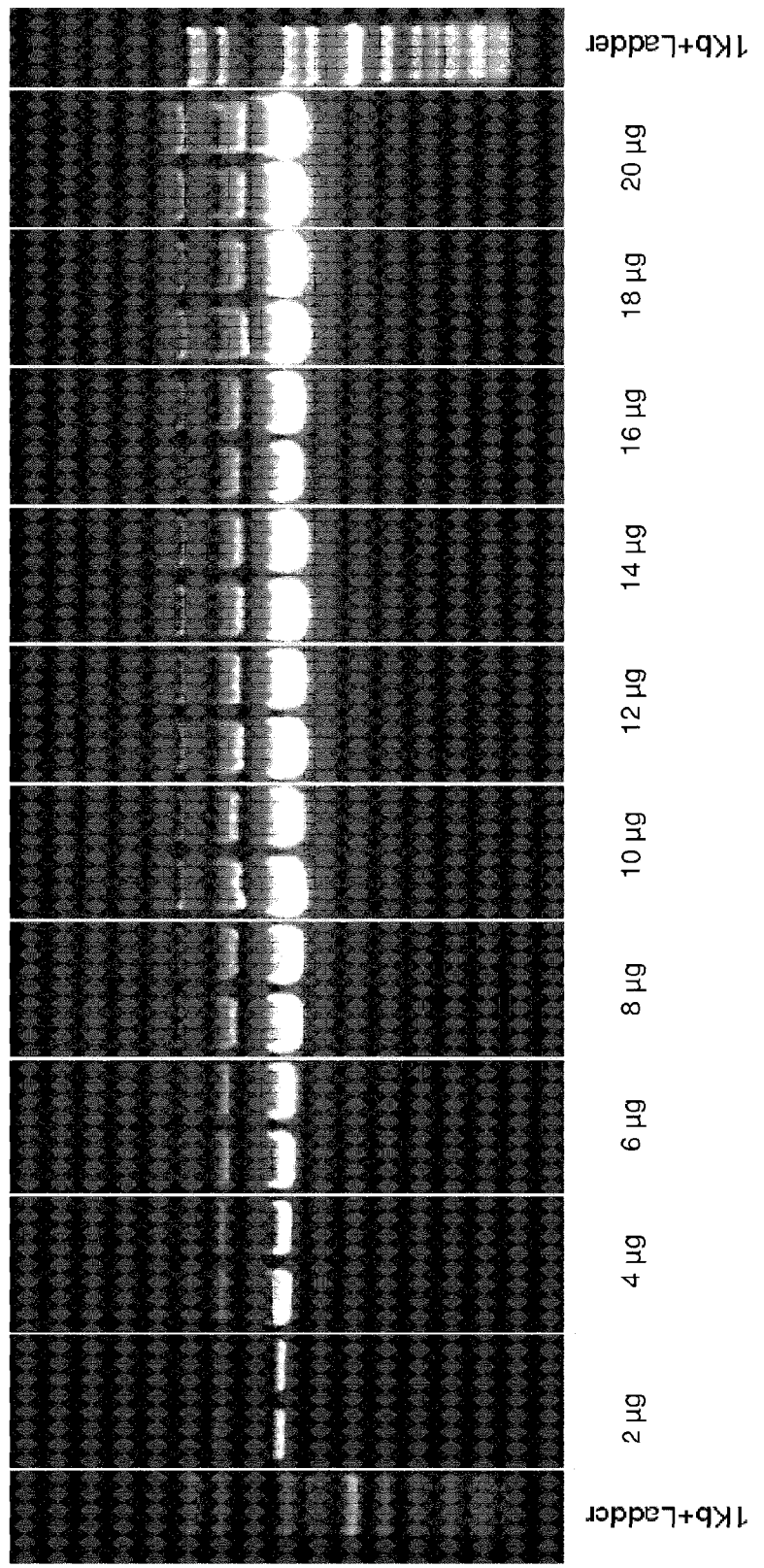

(51) Int. Cl.
*C12N 15/10* (2006.01)
*C04B 35/628* (2006.01)
*C01G 49/06* (2006.01)
*C01G 49/08* (2006.01)
*C09C 3/06* (2006.01)
*C09C 1/24* (2006.01)
*C09C 1/30* (2006.01)

(52) U.S. Cl.
CPC .. *C04B 35/62807* (2013.01); *C04B 35/62849* (2013.01); *C09C 1/24* (2013.01); *C09C 1/3054* (2013.01); *C09C 3/063* (2013.01); *C01P 2004/61* (2013.01); *C01P 2004/62* (2013.01); *C01P 2006/42* (2013.01)

(58) Field of Classification Search
USPC ............... 428/403, 404, 701; 423/335, 339
See application file for complete search history.

(56) References Cited

U.S. PATENT DOCUMENTS

| | | | |
|---|---|---|---|
| 4,112,032 | A | 9/1978 | Blaszyk et al. |
| 4,221,578 | A | 9/1980 | Shoup et al. |
| 4,781,982 | A | 11/1988 | Musselman et al. |
| 5,705,628 | A | 1/1998 | Hawkins |
| 7,183,002 | B2* | 2/2007 | Sauer ............ B03C 1/01 424/490 |
| 2003/0148101 | A1* | 8/2003 | Sauer ............ B03C 1/01 428/404 |
| 2006/0188876 | A1 | 8/2006 | Kilaas et al. |
| 2010/0009375 | A1 | 1/2010 | Sherman et al. |
| 2011/0186524 | A1* | 8/2011 | Sauer ............ B03C 1/01 210/695 |
| 2011/0319506 | A1 | 12/2011 | Erbacher et al. |
| 2012/0245337 | A1 | 9/2012 | Fabis et al. |

FOREIGN PATENT DOCUMENTS

| | | |
|---|---|---|
| DE | 10 2008 063 003 A1 | 6/2010 |
| EP | 0 389 063 A2 | 9/1990 |
| EP | 0 757 106 A2 | 2/1997 |
| EP | 0 880 537 B1 | 12/2004 |
| GB | 2 042 574 A | 9/1980 |
| JP | 47-585 A | 1/1972 |
| WO | 93/10162 A1 | 5/1993 |
| WO | 95/21849 A1 | 8/1995 |
| WO | 96/41811 A1 | 12/1996 |
| WO | 98/31461 A1 | 7/1998 |
| WO | 01/71732 A2 | 9/2001 |
| WO | 2008/058996 A2 | 5/2008 |
| WO | 2010/072821 A1 | 7/2010 |
| WO | 2010/072834 A1 | 7/2010 |

OTHER PUBLICATIONS

International Search Report dated Apr. 24, 2014 for corresponding International Application No. PCT/EP2013/076150, 4 pages.
Plueddeman, *Silane Coupling Agents: Second Edition*, New York and London, Plenum Press, 2013, pp. 82-83.
Rouquerol et al., "Recommendations for the characterization of porous solids," *Pure & Appl. Chem.*, 66(8): 1739-1758, 1994.
Shoup, "Controlling Pore Silica Bodies Gelled From Silica Sol-Alkali Silicate Mixtures," in Kerker (ed.), *Colloid and Interface Science V3: Adsorption, Catalysis, Solid Surfaces, Wetting, Surface Tension, and Water*, Elsevier, 2012, pp. 63-69.
Japanese Office Action for related Application No. JP 2015-546059, English translation (12 pages), dated Aug. 29, 2017.

* cited by examiner

PREPARATION OF SILICA PARTICLES

FIELD OF THE INVENTION

The present invention relates to methods of preparing porous silica particles by deposition of $SiO_2$ onto core particles and in particular describes a method of preparing magnetic silica particles and the use of said magnetic silica particles for isolating nucleic acids.

BACKGROUND OF THE INVENTION

Solid silica materials of various compositions and properties are available to facilitate purification, separation and detection of various molecules. In particular magnetic silica particles are used, because magnetic particles can be collected or retrieved by applying an external magnetic field to a vessel containing the particles. Unbound molecules and supernatant liquid can be separated from the particles or discarded, and the molecules bound to the particles may be retrieved e.g. by elution. Thus, magnetic particles provide relatively rapid, easy, and simple means to purify or separate molecules of interest such as nucleic acids from a liquid phase or a mixture of other molecules. Methods that are based on the use of silica particles are finding increasingly more applications in the purification or isolation of biomolecules, such as nucleic acids and proteins.

Therefore, there is a need for inexpensive and simple production methods for producing silica particles, in particular magnetic silica particles.

For the preparation of silica particles several methods are described in prior art:

DE 10 2006 054 173 describes a method for producing magnetic silica particles that is based on the use of magnetic core particles, a silica salt, a pH modifier, an organic pore forming agent and spray-drying. The produced silica particles exhibit good nucleic acid binding properties. However, spray-drying based methods as are described in said document are very costly due to the required equipment and the costs that accrue during operation of the spray dryer. Furthermore, spray dryer maintenance costs are often high, e.g. because the nozzles of the spray dryer can clog and other problems. Therefore, cost-efficient methods are desirous that allow the production of silica particles that are not based on spray-drying.

WO 1996/041811 describes the preparation of magnetic particles with an outer glass surface that are substantially pore free, or that have pores with less than 10 nm diameters. The particles are prepared by a gel-sol process by hydrolyzing tetraethyl orthosilicate in the acidic milieu. Once the gel is formed it is dried and densified by means of a thermal process to form glass.

WO 1998/031461 describes siliceous oxide-coated magnetic particles having a high resistance to leaching of the magnetic material on exposure to aqueous acidic environments. Disclosed is the preparation of the particles by deposition of siliceous oxide on core particles, wherein a siliceous source (preferably sodium silicate) and an acid (preferably a mineral acid) are added to the suspension containing the core particles. U.S. Pat. No. 6,027,945 describes the use of similar particles for the isolation of nucleic acids.

EP 0 757 106 describes magnetic silica particles comprising a superparamagnetic metal oxide. The particles are prepared by adding $Fe_3O_4$ particles to a tetraethoxysilane/alcohol solution. The deposition is started by adding a hydrolytic catalyst for tetraethoxysilane, which can be a weak or strong acid.

WO 2001/071732 discloses the preparation of porous magnetic silica particles by deposition of silicate onto magnetic core particles, wherein the source of silica can be a tetraalkoxysilane. The primary particles may form aggregates, thereby providing larger particles having a size of about 5 to 25 μm and having a favourable porous structure. The described particles have a good binding capacity for nucleic acids.

Thus, generally, silica is prepared industrially on large scale using two methods. One method is based on the hydrolysis of tetraalkoxysilane from an aqueous composition by the addition of a base or acid. The other method is based on acidifying a strong alkaline silicate composition. If these methods are performed in the presence of core particles, said core particles serve as nucleation sites for the deposited silica. When using magnetic core particles, such as for example iron oxide particles, magnetic silica particles are provided wherein the magnetic core particles are coated and thus are encapsulated by the deposited silica. Larger particles are usually formed by agglomeration of the coated core particles and potentially further coating of the formed aggregates.

When acidifying a silicate solution, the pH value is usually reduced from at least pH 12 to below 11. Thereby, the silicate becomes protonated, thereby providing silicic acid, which precipitates as $SiO_2 \times n\ H_2O$. It is mandatory to perform said process very slowly and in a large dilution, as otherwise the silicic acid precipitates spontaneously, thereby aggravating the production of defined, uniform particles. Still, when preparing magnetic silica particles by said method, there is a risk that aggregates having a very large particle diameter are prepared or that unmagnetic particles, so-called "fines" are provided, which are created by spontaneous hydrolysis and precipitation of silica, wherein said silica, however, is not deposited onto the magnetic core particles, thereby rendering unmagnetic silica particles. Therefore, the quality of the respectively produced silica particles is often not acceptable or a removal of deficient particles is required.

Thus, these prior art methods for preparing silica particles possess several disadvantages, such as the use of costly compounds (especially the tetraalkoxysilanes) or the disability to properly control the deposition process in order to generate particles of a relative uniform size. Spray drying based prior art methods for producing silica particles have the further disadvantage that the required equipment and the operation costs are expensive.

U.S. Pat. No. 3,678,144, U.S. Pat. No. 4,112,032 and U.S. Pat. No. 4,221,578 describe the production of silica bodies from silicate compositions. In the described methods, organic gelation agents such as formaldehyde, paraformaldehyde, formamide or glyoxal are added to the silicate solution which has a high pH value. Said organic gelation agents act as pH modulators. They uniformly dissolve in the silicate solution and react very slowly and uniformly throughout the solution, thereby continuously decreasing the pH value. Said decrease in the pH value of the reaction composition leads to a polymerization and thus precipitation of silica. Also Shoup in Coll. Interf. Sci. 1976, 3, 63-69 "Controlled pore silica bodies gelled from silica sol-alkali silicate mixtures" describes a respective method which involves the use of pH modulators to slowly reduce the pH value of the reaction composition, thereby precipitating silica in a controlled fashion. Here, a mixture of colloidal silica and alkali silicate is used in the reaction composition. Silica is precipitated by acidic hydrolysis of the silicate, the production of silicic acid, elimination of water and subsequent deposition of the silica onto the surface of colloidal silica particles, which provide as core particles a nucleation site for the precipitated silica. It is described that the colloidal silica remains as a stable dispersed phase in the reaction composition and serves as nucleation or growth site for polymerization of the molecular silicate. In this method, acidic hydrolysis of the silicate is achieved by adding a pH modulator. According to one embodiment, formamide is added as pH modulator, which is then hydrolysed to ammonium formate. The silica deposition on the surface of the colloidal core particles results in the formation of aggregates, wherein the primary core particles that are coated with the silica grow together thereby forming the silica body. The resulting pores are defined by the cavities between the particles which adhere due to the deposited silica. The shape of the formed silica body is determined in all said methods by the container in which the silicate solution is gelled. It is described that the formation of controlled pore bodies with narrow pore size distributions as described in the respective documents involve nucleation. Said silica production process which is based on the use of pH modulators is described in said documents only for the production of compact silica bodies which have the shape of the container the production process is performed in. The production of discrete silica particles is not described therein. Furthermore, the inventors found that it was not possible to produce discrete particles when following the respective teachings.

It is the object of the present invention to provide a method of preparing silica particles, in particular magnetic silica particles, which overcome the above mentioned disadvantages. In particular, it is the object of the present invention to provide a cost-efficient method which allows the production of silica particles, in particular magnetic silica particles, which have a high binding capacity for biomolecules, in particular nucleic acids.

SUMMARY OF THE INVENTION

The inventors found that a method that is based on the use of a silicate salt and a pH modulator in combination with specific reaction conditions which involve the addition of a base to the reaction composition results in a controlled $SiO_2$ deposition process which yields discrete silica particles having excellent adsorption characteristics. Said method is suitable for producing magnetic silica particles.

Thus, according to a first aspect, a method is provided for producing particles having a $SiO_2$ containing surface said method comprising:
a) providing an aqueous reaction composition comprising
 i) core particles,
 ii) a silicate salt,
 iii) a base, and
 iv) a pH modulator
wherein the pH value of the reaction composition is above the gelation pH value of the silicate salt;
b) agitating said reaction composition, wherein the pH modulator decreases the pH value of the reaction composition and wherein due to said decrease of the pH value of the reaction composition $SiO_2$ is deposited onto the core particles, whereby particles are formed which have a diameter of 30 μm or less; and
c) obtaining the particles.

As is shown by the examples, said method allows the production of discrete silica particles and also allows to produce magnetic silica particles. The production process is very cost-efficient, can be scaled-up and in contrast to prior art methods is less susceptible to handling errors. Furthermore, no expensive equipment such as a spray dryer is required. More than 50% of the production costs can be saved compared to prior art methods. Therefore, the present invention makes an important contribution to the prior art.

According to a second aspect, the present disclosure provides porous silica particles having a size of 30 μm or less, which are formed by agglomerated $SiO_2$ coated core particles, wherein the core particles are essentially encapsulated by the $SiO_2$ coating and wherein the silica particles have a composition regarding the comprised $SiO_2$ and core particles that is 15 to 75% (by weight) core particles and 25% to 85% (by weight) $SiO_2$, and wherein the silica particles are capable of binding at least 12.5 μg nucleic acid molecules per mg particles.

Silica particles having a respective high nucleic acid binding capacity can be advantageously used for isolating nucleic acids. Respective silica particles can be prepared by the method according to the first aspect.

According to a third aspect, the present invention pertains to the use of silica particles according to the second aspect or produced according to the method according to the first aspect, for isolating biomolecules, in particular for isolating nucleic acids from various samples. As is shown by the examples, the silica particles produced by the method according to the present invention have a high nucleic acid binding capacity. Preferably, magnetic silica particles are used.

Other objects, features, advantages and aspects of the present application will become apparent to those skilled in the art from the following description and appended claims. It should be understood, however, that the following description, appended claims, and specific examples, while indicating preferred embodiments of the application, are given by way of illustration only. Various changes and modifications within the spirit and scope of the disclosed invention will become readily apparent to those skilled in the art from reading the following.

FIGURES

FIG. 1: Gelelectrophoretic analysis of plasmid DNA (2 to 20 μg pUC21) purified with magnetic silica particles using a chaotropic binding buffer (for details see Example 6).

Figure 2:
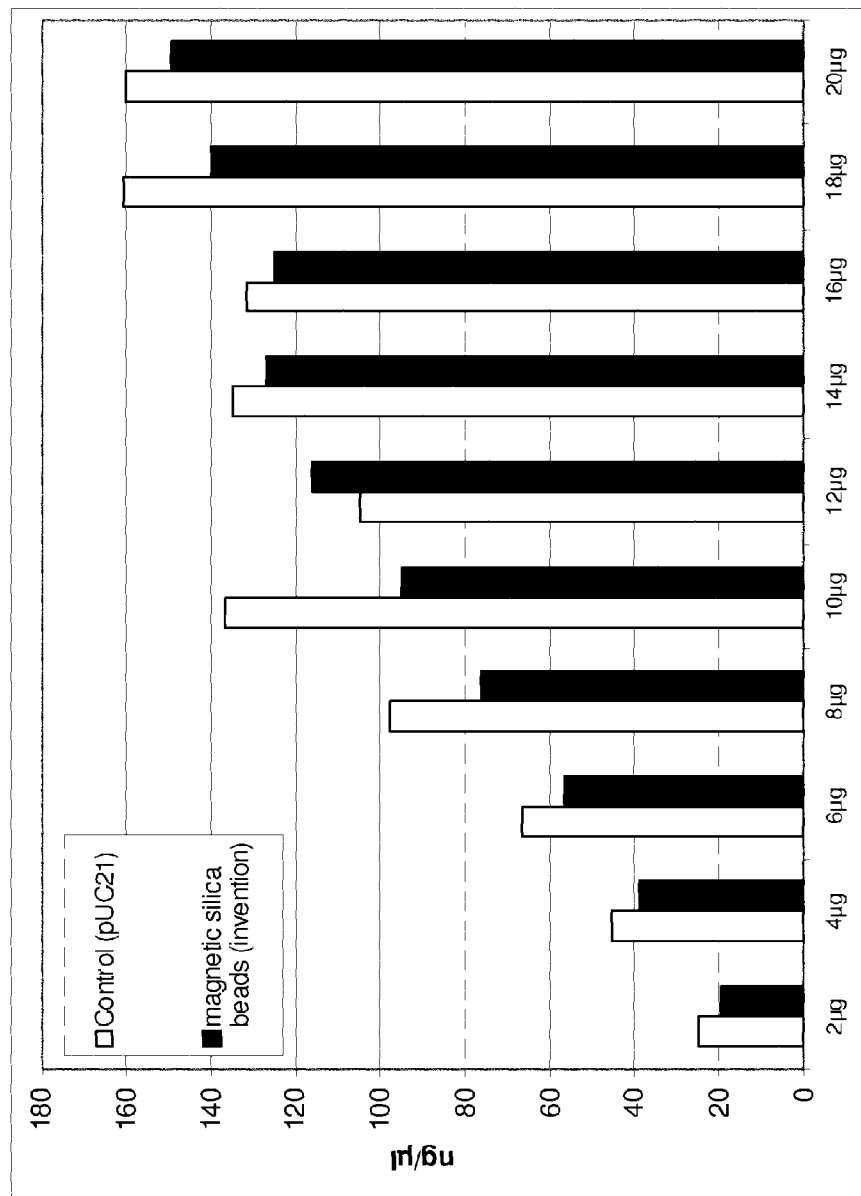

FIG. 2: Photometric quantification of plasmid DNA (2 to 20 μg pUC21) purified with magnetic silica particles using a chaotropic binding buffer (y-axis: DNA concentration in ng/μl; for details see Example 6).

Figure 3:
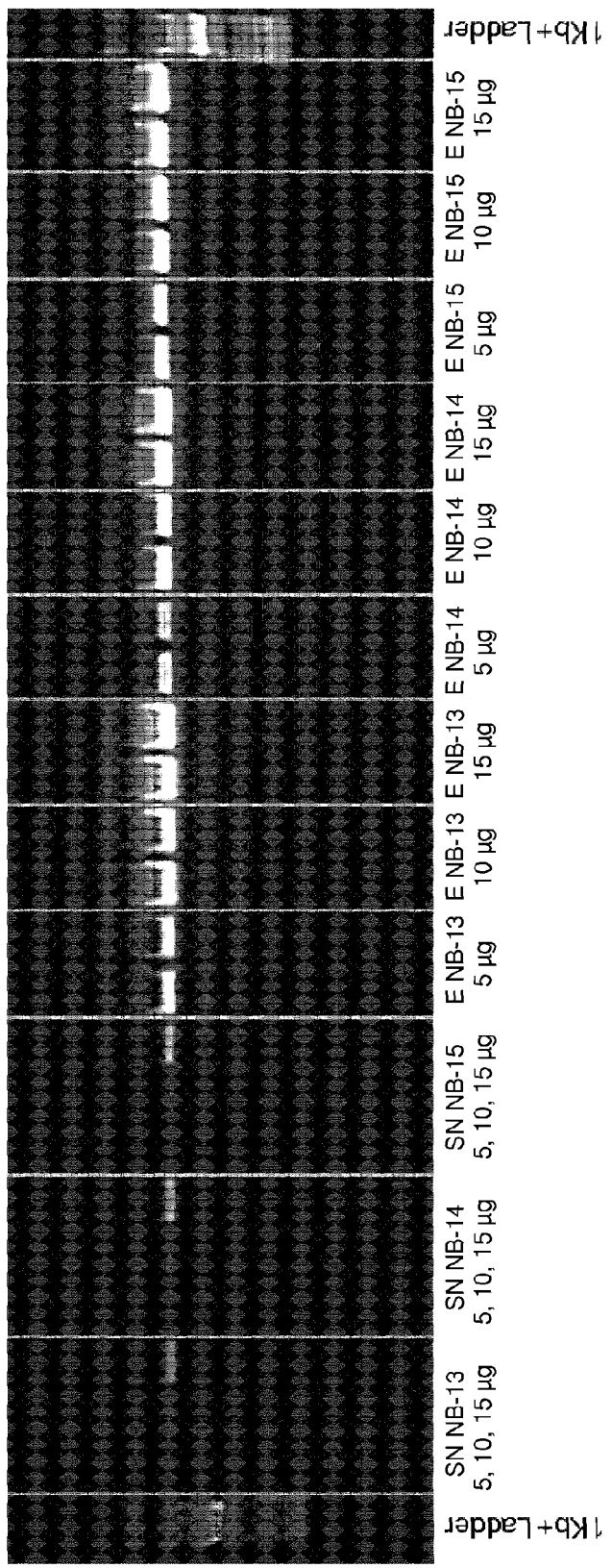

FIG. 3: Gelelectrophoretic analysis of plasmid DNA (2 to 20 μg pUC21) purified with magnetic silica particles modified with an anion exchanger (for details see Example 7).

Figure 4:
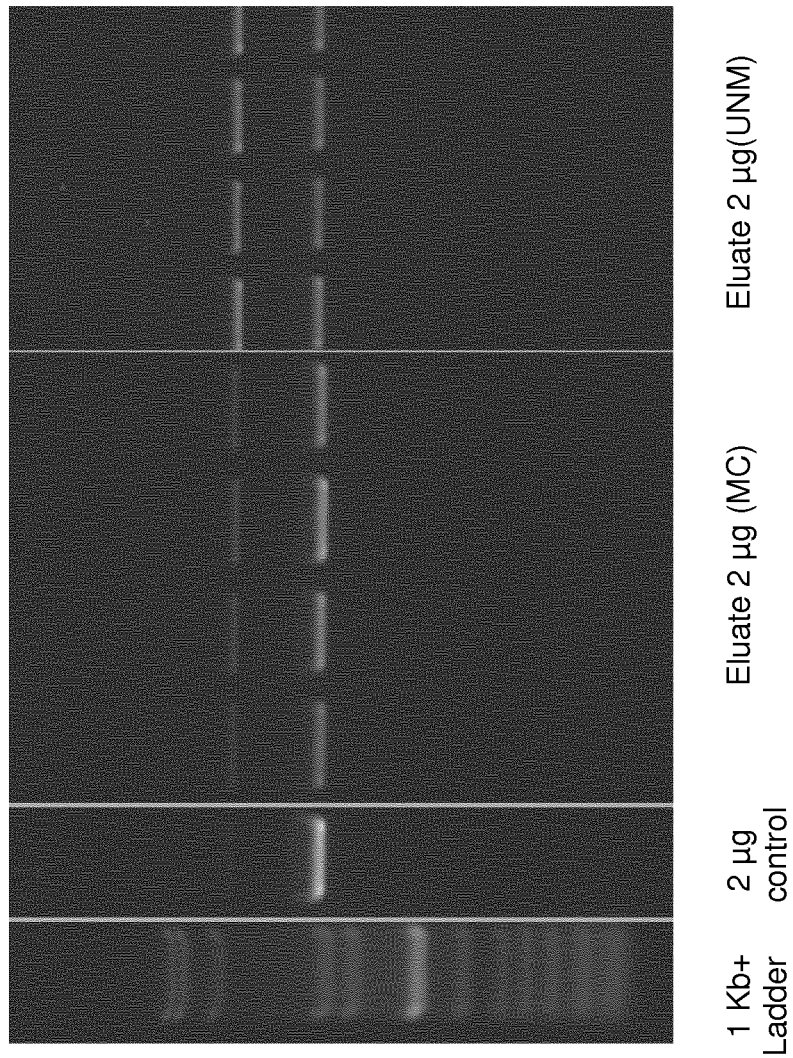

FIG. 4: Gelelectrophoretic analysis of plasmid DNA (2 to 20 μg pUC21) purified with unmodified magnetic silica particles (UNM) vs. carboxylated silica particles (MC; for details see Example 8).

DETAILED DESCRIPTION OF THE INVENTION

According to a first aspect, a method is provided for producing particles having a $SiO_2$ containing surface wherein said method comprises:
a) providing an aqueous reaction composition comprising
 i) core particles,
 ii) a silicate salt, iii) a base, and
iv) a pH modulator
wherein the pH value of the reaction composition is above the gelation pH value of the silicate salt;
b) agitating said reaction composition, wherein the pH modulator decreases the pH value of the reaction composition over time and wherein due to said decrease of the pH value of the reaction composition $SiO_2$ is deposited onto the core particles, whereby particles are formed which have a diameter of 30 μm or less; and
c) obtaining the particles.

In particular, a method for producing particles having a $SiO_2$ containing surface is provided comprising:
a) providing an aqueous reaction composition comprising
i) core particles,
ii) an added base,
iii) a silicate salt, and
iv) a pH modulator
wherein the pH value of the reaction composition is above the gelation pH value;
b) agitating said reaction composition, wherein the pH modulator is an organic compound that reacts in the alkaline milieu of the reaction composition, thereby decreasing the pH value of the reaction composition over time and wherein due to said decrease of the pH value of the reaction composition $SiO_2$ is deposited onto the core particles, whereby particles are formed which have a diameter of 30 μm or less; and
c) obtaining the particles.

The method, its individual steps and preferred embodiments will now be explained in detail.

In step a), an aqueous composition is provided which comprises several components i) to iv) which will subsequently be explained in detail.

The Core Particles

The reaction composition comprises as component i) core particles. The core particles serve as nucleation sites for $SiO_2$ which is deposited in step b). Preferably, the core particles have a median diameter that lies in a range of 5 nm to 200 nm, 8 nm to 150 nm or 10 nm to 100 nm. According to one embodiment, the median diameter lies in a range of 10 nm to 60 nm. Several materials are suitable for providing the core particles and the choice of the core particles also influences the properties of the produced silica particles. According to one embodiment, the core particles comprise or consist of silicon dioxide. E.g. colloidal silica particles can be used as core particles. Core particles may also comprise or consist of a polymeric material. Also composite core particles comprising different materials, e.g. arranged in layers can be used.

In one aspect the core particles comprise or consist of an oxide, in particular a semimetal oxide or a metal oxide.

If core particles having magnetic properties are used, the produced silica particles also exhibit magnetic properties in the presence of a magnetic field. Because magnetic silica particles have significant advantages regarding their handling, it is preferred to use core particles which have magnetic properties. Core particles have magnetic properties if they are at least magnetic in the presence of a magnetic field and thus can be moved by the aid of a magnetic field. E.g. the core particles may have superparamagnetic, paramagnetic, ferrimagnetic or ferromagnetic properties. The use of superparamagnetic or paramagnetic core particles is preferred.

According to one embodiment, the core particles comprise or consist of a metal oxide. Preferably, the metal oxide has magnetic properties. Preferably, the core particles comprise or consist of iron oxide. The iron oxide particles may be, e.g., provided by $Fe_2O_3$ (hematite), $\gamma$-$Fe_2O_3$ (maghemite), $Fe_3O_4$ (magnetite) or a combination of the foregoing materials. Preferably, iron oxide particles are used which have superparamagnetic properties. Iron oxide crystals of less than about 30 nm in diameter are capable of exhibiting superparamagnetic properties. In one embodiment, the magnetic core particles comprise a metal oxide with divalent cations such as Co, Mn, Sr, Ba, Zn, Mg, Ti, Zr as well as combinations thereof and/or combinations with iron oxide.

According to one embodiment, hollow core particles are used. The use of hollow core particles has a strong influence on the sedimentation characteristics of the obtained silica particles. Hollow core particles can be prepared e.g. by depositing silica onto a core material, e.g. a polymeric core having a hydrophilic surface and subsequent removal of the core material, e.g. by THF. Thereby, hollow silica particles are provided that can be used as core particles in the method of the present invention. Furthermore, magnetic hollow core particles can also be used. E.g. magnetic material can be incorporated in or deposited onto the hollow silica core particles, thereby providing magnetic hollow silica core particles. E.g. if the hollow silica core particles are porous, they can be impregnated with magnetic pigments as is e.g. described in WO 93/10162 thereby providing magnetic hollow core particles. As subsequently $SiO_2$ is deposited onto said magnetic hollow core particles, the magnetic material becomes encapsulated into the silica coating thereby preventing leaching of the magnetic material. Producing magnetic silica particles having a slow sedimentation profile is advantageous when using the particles for isolating biomolecules such as nucleic acids.

The magnetic core particles can be prepared in situ.

In one embodiment, magnetic core particles are used which consist of iron, copper, nickel or alloys thereof. In one embodiment, the core particles are composite particles, such as a composite of a metal and a metal oxide, more preferably an iron particle with a magnetite coating.

In one embodiment of the invention, the core particles consist of magnetite and preferably have superparamagnetic properties.

According to one embodiment, the amount of core particles in the reaction composition is 20% or less, 15% or less, 10% or less or 7.5% or less. The amount of core particles in the reaction composition also depends on the desired or acceptable degree of agglomerate formation.

It is within the scope of the present invention to directly add core particles such as e.g. iron oxide particles, e.g. magnetite, to the reaction composition. Respective core particles are commercially available. They can also be processed, e.g. ground to the desired size.

Preferably, stabilized iron oxide particles are used as magnetic core particles. In one embodiment of the invention, the iron oxide core particles are stabilised by a surfactant, a phospholipid or an organic acid or salt thereof. In one embodiment, the iron oxide core particles are stabilized by a carboxylic acid such as citric acid or a salt thereof. In a preferred embodiment, magnetite core particles stabilised by citrate are used. It is assumed that the presence of a respective stabilizer supports the separation of the iron oxide core particles and thereby reduces the unwanted aggregation of the iron oxide particles in the reaction composition. Also other anions of carboxylic acids, in particular of dicarboxylic acids, tricarboxylic acids or polycarboxylic acids can be used as respective stabilizers, examples include but are not limited to polyacrylic acid, polymethacrylic acid and carboxymethyl dextrane.

According to one embodiment, core particles are produced prior to step a). E.g. core particles comprising iron oxide can be prepared by adding iron salts, preferably iron(III)chloride and iron(II)chloride, to an aqueous alkali hydroxide solution such as a KOH solution and precipitating iron oxide particles out of said solution. Alternatively, iron-acetylaceton complexes can be heated to provide iron oxide particles. The respectively obtained iron oxide particles can be stabilized as described above. Preferably, they are stabilized by citrate. According to one embodiment, production of the iron oxide core particles occurs in the presence of a protective gas such as nitrogen in order to prevent oxidation.

According to one embodiment, the produced iron oxide particles are maintained in contact with an aqueous medium from the moment of their precipitation through the deposition of the silica coating thereon. According to one embodiment, the obtained iron oxide core particles can be directly coated with $SiO_2$ in the reaction composition without prior isolation or purification of the produced iron oxide particles.

According to one embodiment, the method of the present invention comprises
- suspending iron oxide core particles, which preferably are stabilized e.g. as described above, in an aqueous solution, preferably water;
- optionally adding a silica salt and/or a stabiliser, preferably a carboxylic acid such as citrate;
- adding potassium hydroxide, potassium silicate and formamide to said core particles containing suspension thereby forming the reaction composition of step a).

The reaction is then continued as described herein until the particle formation is completed. A respective production of magnetic silica particles provides magnetic particles of a uniform size which have a high binding capacity for biomolecules such as nucleic acids. Using preformed, stabilized iron oxide core particles as described above is advantageous because salts that might have formed during the iron oxide preparation were, respectively can, be removed and thus, do not support the aggregation of the core particles in the reaction composition.

According to one embodiment, a thin layer of $SiO_2$ is deposited onto the core particles prior to adding the base and the pH modulator. It is assumed that the pre-deposition of silica is favourable and supports the subsequent deposition of the $SiO_2$ coating.

According to one embodiment, the method of the present invention comprises
- preparing iron oxide core particles by adding one or more iron salts, preferably iron(III)chloride and iron(II)chloride, to an aqueous alkali hydroxide solution, preferably to an KOH solution, to precipitate magnetite or maghemite as core particles; and
- adding potassium hydroxide, potassium silicate and formamide to said core particles containing solution thereby forming the reaction composition of step a).

The reaction is then continued as described herein until the particle formation is completed. A respective production of magnetic silica particles is very cost efficient and provides magnetic particles which have a high binding capacity.

The Silicate Salt

The reaction composition comprises as component ii) a silicate salt. Since silica itself is essentially insoluble in water, the silica is added in the form of a soluble silicate salt. Using a silicate salt as silica source is advantageous because silicate salts are inexpensive, thus rendering the production method inexpensive. In contrast to prior art methods, the silicate concentration is low in the method of the present invention. In particular, the silicate salt concentration is such, that there is no spontaneous $SiO_2$ precipitation. In order to yield a controlled and efficient deposition of $SiO_2$ on the core particles and to allow the formation of discrete silica particles, it is preferred that $SiO_2$ originating from the silicate salt is comprised in the reaction composition in a concentration of less than 1 mol/l. Therefore, preferably, the silicate salt is present in the reaction composition in a concentration of less than 1 mol/l. It was found that reducing the $SiO_2$ and thus the silicate salt concentration in the reaction composition, while maintaining a high pH value preferably at 12.5 or above due to the addition of the base, is favourable for the formation of discrete small particles which have good binding properties for biomolecules such as nucleic acids. According to one embodiment, the reaction composition comprises $SiO_2$ originating from the silicate salt in a concentration that lies in a range selected from 0.01 to 0.9 mol/l, 0.02 to 0.7 mol/l, 0.03 to 0.6 mol/l, 0.04 to 0.5 mol/l, 0.05 to 0.4 mol/l, 0.06 to 0.3 mol/l, 0.07 to 0.2 mol/l and 0.09 to 0.15 mol/l. According to one embodiment, the silicate salt concentration in the reaction composition lies in a range selected from 0.01 to 0.9 mol/l, 0.02 to 0.7 mol/l, 0.03 to 0.6 mol/l, 0.04 to 0.5 mol/l, 0.05 to 0.4 mol/l, 0.06 to 0.3 mol/l, 0.07 to 0.2 mol/l and 0.09 to 0.15 mol/l.

Suitable silicate salts include but are not limited to ammonium silicates, alkali metal silicates, silicates of substituted ammonium salts, such as tetramethyl ammonium hydroxide, alkali earth metal silicates, and earth metal silicates. In principle, any alkali-soluble silicate can be used. According to one embodiment, an alkali metal silicate salt is used. Examples include sodium or potassium silicate or a mixture thereof. According to a preferred embodiment the silicate salt is a potassium silicate. The use of potassium silicate is advantageous because the potassium ion has an advantageous influence on the properties of the deposited silica and thus the formed silica particles. According to one embodiment, the potassium silicate salt is of the formula $K_2O \cdot nSiO_2$, whereby n is between 1.0 and 5.0, and preferably is between 2.0 and 3.0. Suitable concentration ranges for the silicate salt are described above.

According to one embodiment, the coating that is deposited onto the core particles consists of $SiO_2$. However, it is also possible to include other compounds, in particular other oxide compounds. In one embodiment, the $SiO_2$ containing coating that is deposited onto the core particles comprises one or more oxide compounds selected from $B_2O_3$, $Al_2O_3$, $TiO_2$, $ZrO_2$, $Na_2O$, $K_2O$, CaO and MgO. A respective coating can be produced by incorporating suitable oxide species into the reaction composition. Suitable methods for incorporating respective oxides into the $SiO_2$ coating that is precipitated out of a silicate solution due to the activity of a pH modulator are described in U.S. Pat. No. 3,678,144 and can be adapted to the method according to the present invention.

The Base and the Initial pH Value of the Reaction Composition

The reaction composition comprises as component iii) a base. The inventors found that it is important to comprise a base in the reaction composition in order to maintain a high pH value when reducing the silicate concentration. The addition of a base ensures that the pH value of the reaction composition is well above the gelation pH value of the silicate. To have an initial pH value that lies at least 0.5 pH units, at least 0.75 pH units, preferably at least 1 pH unit and more preferred at least 1.5 pH units above the gelation point of the silicate is favorable for the deposition result. In particular, an uncontrolled precipitation of silica from the reaction composition and in particular a silica precipitation without contact to core particles is prevented thereby. A larger distance of the initial pH value of the reaction composition to the gelation pH value of the silicate ensures that it takes time before the gelation pH value is reached due to the activation of the pH modulator. This allows to achieve a thorough resuspension and mixture of all components comprised in the reaction composition, in particular of the core particles in the reaction composition, before the gelation pH value is reached and thus before the silica deposition process starts. Thereby it is ensured that the silica precipitates and/or adsorbs slowly and in a controlled fashion onto the resuspended core particles. This can be particularly achieved when reducing the amount of $SiO_2$ in the reaction composition as described above, e.g. to 1 mol/l or less, more preferred to 0.75 mol/l or less.

The initial pH value of the reaction composition is sufficiently high in order to activate the used pH modulator e.g. by an alkaline hydrolysis of the pH modulator as will be explained in the next section. Thus, the initial pH value also depends on the pH modulator used. E.g. while high initial pH values of 12.5 or above, preferably 13 or above are preferred when using compounds such as formamide as pH modulator, lower pH values can be used when using other pH modulators such as urea.

The base is included, respectively is added to the reaction composition to adjust the pH value of the reaction composition to the initial pH value. Any strong base can be used which is capable of adjusting the initial pH value to the desired high pH value. E.g. ammonia can be used. Preferably, an inorganic base such as alkali hydroxide is used, e.g. NaOH or KOH. The use of KOH as base is preferred because it was found that KOH provides a very homogeneous reaction composition and favorable influences the deposition result. Furthermore, the potassium cation—originating from the base and/or the silica salt—is favourable regarding the pore size. In particular, the use of potassium is favourable because of its lower charge density and its large hydration sphere, which stabilizes the suspension and slows down the destabilization process.

According to one embodiment, the initial pH value of the reaction composition is selected from pH 11 or above, pH 11.5 or above, pH 11.75 or above, pH 12 or above, pH 12.25 or above, pH 12.5 or above, pH 12.75 or above, pH 13 or above, pH 13.25 or above, pH 13.5 or above, pH 13.75 or above and pH 14 or above. Thus, the pH value of the reaction composition may e.g. lie in a range between 11.5 to 15, 12 to 14, 12.5 to 14 or 13 to 14 or may have any value within these ranges. As discussed, the initial pH value of the reaction composition can be adjusted to these high pH values by the addition of the base, preferably KOH, and preferably is selected from pH 12.5 or above, pH 12.75 or above, pH 13 or above, pH 13.25 or above, pH 13.5 or above and pH 14 or above.

The pH Modulators

The reaction composition comprises as component iv) a pH modulator. The pH modulator comprised in the reaction composition slowly reduces the pH value of the reaction composition by a chemical reaction. As defined in claim 1 step b), the reaction composition is agitated, e.g. stirred, and the pH modulator slowly and uniformly decreases the pH value of the reaction composition. Due to said slow and uniform decrease of the pH value of the reaction composition that is induced by the pH modulator, $SiO_2$ is deposited onto the core particles in a controlled fashion, whereby discrete small particles are formed.

The term "pH modulator", as used herein, in particular refers to an organic compound that reacts in the alkaline milieu of the reaction composition, thereby decreasing the pH value of the reaction composition over time. The initial pH value of the reaction composition is so high that the pH modulator is activated and thus reduces the pH of the reaction composition. E.g. the pH modulator can be hydrolysed at the initial high pH value of the reaction composition to result in an acidic compound. The acidity of the resulting acidic compound decreases the pH value of the reaction composition down to the gelation pH value at which $SiO_2$ precipitates and accordingly is deposited onto the core particles comprised in the reaction composition. Also more than one pH modulator can be used. The use of one or more pH modulators ensures a slow and uniform decrease of the pH value, thereby preventing a disadvantageous spontaneous hydrolysis of the silicate and thus precipitation of $SiO_2$. As the reaction composition is continuously agitated during the deposition of the silica, it is ensured that the core particles remain in suspension thereby ensuring that $SiO_2$ is uniformly deposited onto the core particles. The reaction composition described herein provides controlled reaction conditions that allow the reliable preparation of discrete silica particles having good binding characteristics as is demonstrated by the examples. The use of a pH modulator in combination with the reaction conditions described herein allows the use of less expensive inorganic silicate salts instead of the expensive and less convenient organic silica derivatives that are commonly used in the prior art in order to produce silica particles on industrial scale. The method of the invention which is based on the use of pH modulators has the advantage that the acidification process of the reaction composition is very slow and controlled, thereby ensuring that the reproducibility of the particle production is not strongly dependent on variations of the added reagents. Therefore, it is preferred to not reduce the pH value of the reaction composition by titration but only by, respectively due to the activity of the pH modulator. The use of the pH modulator reduces the deposition speed what improves the $SiO_2$ deposition onto the core particles and provides small, discrete particles which have good binding characteristics.

Reaction mechanisms for producing said acidic compound from the pH modulator which decrease the pH value of the reaction composition include e.g. the hydrolysis of the organic compound to yield a carboxylic acid or the oxidation of an aldehyde to a carboxylic acid. In case of an aldehyde, a disproportion reaction (Cannizzaro reaction), which can also be performed intramolecularly (e.g. for dialdehydes such as glyoxal) can be responsible for the formation of the carboxylic acid. According to one embodiment, organic gelation agents are used as pH modulators. According to one embodiment, the pH modulator is an organic compound comprising an ester, an amide, an aldehyde or a polyoxymethylene group. The polyoxymethylene group containing compound preferably represents a polycondensation product of an aldehyde. Suitable pH modulators may be selected from the group consisting of formaldehyde, paraformaldehyde, formamide, glyoxal, methyl formate, methyl acetate, ethyl formate, ethyl acetate, alkyl halogenide, acid amides such as acetamide, acid esters, glutardialdehyde and urea. Suitable pH modulators that can be used for the purpose of the present inventions are also disclosed in U.S. Pat. No. 4,221,578 and U.S. Pat. No. 3,678,144. Hydrolysis of the pH modulator reduces the pH value of the reaction composition during the reaction. According to a preferred embodiment, formamide is used as pH modulator due to its high reactivity and high convenience in handling the compound. Formamide is hydrolysed at high pH values, preferably at pH 13 or above, thereby providing ammonium and formiate and slowly decreasing the pH value of the reaction composition over time.

The pH modulator can be used in a wide concentration range. The amount will also depend on the type of and thus the reactivity of the pH modulator used. Suitable concentration ranges include but are not limited to 0.01 to 4 mol/l, 0.1 to 3 mol/l, 0.2 to 2.5 mol/l, 0.3 to 2 mol/l, 0.4 to 1.5 mol/l and 0.5 to 1 mol/l. Formamide is more reactive than certain other pH modulators and thus can be used in lower concentrations. In a preferred embodiment formamide is used as pH modulator whereby the formamide concentration in the reaction composition is in a range between 0.01 and 2 mol/l, 0.1 to 1.5 mol/l, 0.2 mol/l to 1.25 mol/l, 0.3 mol/l to 1.0 mol/l, 0.4 to 0.8 mol/l and 0.5 to 0.7 mol/l and wherein preferably, the initial pH value is at least 12.5 and more preferred at least 13.

According to one embodiment, the ratio of pH modulator to silicate salt lies in a range of 5:1 to 20:1, 7.5:1 to 15:1 or 10:1 to 13:1. According to one embodiment, the ratio of pH modulator to silicate salt, preferably formamide to potassium silicate, is approx. 11:1.

The pH value of the reaction composition is reduced by the pH modulator, e.g. due to its alkaline hydrolysis. According to one embodiment, the initial pH value of the reaction composition is decreased at least by 1 pH unit, preferably at least by 1.5 pH units, more preferred at least by 2 pH units, more preferred at least by 2.5 pH units and most preferred at least by 3 pH units. Thereby, the $SiO_2$ deposition onto the core particles occurs in a controlled fashion. As the reaction composition is continuously agitated, e.g. stirred, during the deposition of the $SiO_2$, the controlled reduction of the pH value leads to very homogeneous deposition results and spontaneous, uncontrolled silica depositions are avoided. Therefore, in contrast to prior art methods, the silica precipitation does not occur within seconds or minutes, but occurs over a prolonged period of time, preferably over at least 1 h, at least 5 h, at least 7 h, at least 8 h, at least 10 h or at least 12 h.

The initial pH value of the reaction composition may be decreased by the acidifying activity of the pH modulator to a pH value of 12.0 or less, 11.5 or less, 11.4 or less, 11.3 or less, 11.2 or less, 11.0 or less, 10.8 or less, 10.7 or less, 10.6 or less, 10.5 or less, 10.4 or less, 10.3 or less or 10.2 or less. Suitable ranges for the decreased pH value at which hydrolysis of the silicate occurs and silica is deposited onto the core particles include 9 to 12, 9.5 to 11.75, 10 to 11.5 and more preferably 10.5 to 11.2.

Process Parameters

In order to ensure a uniform deposition of $SiO_2$ onto the core particles and the formation of discrete silica particles of the desired size it is important to continuously agitate the reaction composition during the deposition of $SiO_2$ and thus during the particle formation. Agitation can be achieved e.g. by stirring, ultrasonification, shaking, bubble stream or any other techniques known to a person skilled in the art.

For depositing the $SiO_2$ containing coating, the core particles or core particle slurry can be dispersed in the reaction composition, which preferably is prepared based on water, such as deionized water. The concentration of core particles in the reaction composition may be varied but is preferably less than 50 g/l.

The core particles, the base, the silicate and the pH modulator can be added in various orders of addition to provide the reaction composition. Preferably, the core particles are provided in an aqueous medium and agitated, preferably stirred, to form a suspension. Then, the base, preferably KOH, is added in an amount to adjust the pH value of the reaction composition to a pH value that lies above the gelation pH of silica. Preferably, the initial pH value is 12.5 or above, preferably 13 or above. Suitable initial pH values and ranges were also described above. Afterwards, the silica salt, preferably an alkali metal silicate, is added. Then, the pH modulator is added. This order of addition is preferred. The reaction composition is preferably continuously stirred while the components are added. Once the pH modulator is added, it will react under the highly alkaline conditions of the reaction composition, e.g. by hydrolysis, thereby slowly decreasing the pH value. Therefore, it is preferred to add the pH modulator after the core particles, the base and the silicate salt were added. According to one embodiment, the pH modulator is the last compound that is added to the reaction composition.

As silica is deposited or precipitated onto the core particles, the $SiO_2$ coated core particles, e.g. the $SiO_2$ coated magnetic core particles begin to agglomerate to form larger, porous silica particles. Thus, the core particles onto which $SiO_2$ was deposited may and preferably form larger agglomerates onto which further $SiO_2$ may be deposited or adsorbed. Thus, the agglomerates themselves may have an additional $SiO_2$ coating on their surface. A silica particle formed by respective agglomerates comprises several core particles. The method according to the present invention allows to control the agglomeration process so that discrete particles of a rather uniform size are provided that exhibit good binding properties as is shown in the examples. The silica particles which are manufactured according to the method of the invention exhibit a large surface area, since they are created by deposition of silica on the core particles and subsequent agglomeration of the so prepared composite particles. This advantageously results in the formation of macropores as interstices.

As described above, in a preferred embodiment of the invention, the initial pH value of the reaction composition is above 12.5 and is decreased due to the acidifying activity of the pH modulator to a pH value of less than 11.2. More preferred, the pH value of the initial reaction composition is between 13 and 14 and is decreased due to the acidifying activity of the pH modulator to a pH value that lies in a range of 10.5 to 11.2. The initial highly basic pH value of the reaction composition is preferably adjusted by using an inorganic base, being preferably an alkali hydroxide such as KOH.

The reaction composition can be agitated at any temperature between the freezing and the boiling point. Deposition of the silica is more rapid as the temperature is increased. In one embodiment of the invention, the reaction composition is agitated, preferably stirred at a temperature between 5 and 50° C., preferably between 10 and 30° C. and more preferably is stirred at room temperature. Agitation is performed according to one embodiment at a temperature below 50° C., preferably below 30° C., more preferred at room temperature.

The reaction composition comprising all components i) to iv) and optionally comprising further compounds can be incubated during stirring for at least 30 min, at least 1 hour, at least 2 hours, at least 5 hours, at least 7 hours, at least 10 hours and more preferably for at least 12 hours. According to one embodiment, the reaction composition is incubated under stirring between 5 and 20 hours, preferably between 10 and 20 hours, 12 and 20 hours and more preferably between 15 and 18 hours, preferably at room temperature. To slowly deposit the $SiO_2$ over such prolonged incubation periods advantageously influences the particle characteristics as described herein and results in the cost-efficient and stable production of particles having uniform characteristics.

In a preferred embodiment of the invention, the core particles are magnetic particles, preferably iron oxide particles, the silicate source used for the deposition is potassium silicate preferably of the formula $K_2O.nSiO_2$ with n between 2.0 and 3.0, the pH modulator is formamide and the initial pH value of the reaction composition is adjusted to a pH of 13 or above by using KOH and the reaction composition is stirred between 10 and 20 hours at room temperature.

The size of the particles can be controlled by variation of certain reaction parameters such as the reaction time, the reaction temperature and the concentration of the reactants. E.g. increasing the ionic strength of the reaction composition, e.g. by increasing the salt concentration, results in larger particles. Furthermore, larger particles and also larger pores can be obtained by using longer reaction times as more $SiO_2$ is deposited. Larger pores are also formed when increasing the ratio of silicate to core particles, as more $SiO_2$ is deposited onto the core particles. This results in larger particles which increases the interstices between the agglomerated small particles that form the larger silica particle. The degree of agglomeration of the silica coated core particles and thus the size of the silica particle that is formed by agglomeration can also be influenced and thus be adjusted by the concentration of the reactants in the composition, the steering speed and the viscosity of the reaction composition.

After the particle formation is completed, and optionally after an aging step, the final particles can be collected either by sedimentation, filtration, decantation centrifugation or by application of a magnetic field in case magnetic silica particles were produced. All or the predominant portion of the liquid supernatant of the reaction composition can be discarded. The particles can be collected in form of a particle suspension. Preferably, the particles are washed several times. The wash solution may contain water, salts and/or organic solvents. E.g. the particles can be washed with water and/or alcohol, e.g. an anhydrous alcohol such as ethanol. The respectively worked-up particles are preferably stored in form of a suspension. They can be stored e.g. in water, buffers or alcohol.

According to one embodiment, no aging and/or drying step is performed. The silica particles produced according to the present invention can be directly used, preferably after they were washed at least once. The method of the invention advantageously does not involve the use expensive equipment such as a spray dryer in order to produce the silica particles.

Modification of the Particle Surface

According to one embodiment, the surface of the obtained silica particles, which preferably are magnetic silica particles, is not further modified. However, it is also within the scope of the present invention to further process the obtained silica particles and e.g. to modify the surface of the particles. Non-limiting examples are described below.

According to one embodiment, the particles are heat treated, e.g. sintered, in order to convert the silica surface to a glass surface.

According to embodiment, the surface of the silica particles, which optionally is a glass surface as described above, is modified, in particular functionalized. E.g. it is within the scope of the present invention to functionalize the silica surface with suitable chemical functionalities and/or ligands which can either specifically or unspecifically bind a target of interest. Targets include but are not limited to biomolecules and other biological material such as cells. Specific functionalities and/or ligands include but are not limited to the functionalization with chemical compounds, nucleic acid probes or biological compounds such as proteins or peptides which are capable of specifically binding a biological material of interest such as e.g. a specific cell. Respective functionalization strategies for silica surfaces are well-known in the prior art and thus, do not need any detailed description here. Non-limiting examples are also described below.

According to one embodiment, the surface of the obtained silica particles is chemically modified in order to generate functional groups on the particle surface. Suitable methods for functionalizing or modifying silica surfaces are well known to the skilled person and thus do not need any further description here.

According to one embodiment, the surface of the particles is modified with ion exchange moieties, e.g. anion exchange moieties or cation exchange moieties or with both types of ion exchange moieties. According to one embodiment, the surface is modified with anion exchange moieties. Anion exchange moieties comprise one or more groups capable of anion exchange such as e.g. amine groups. Under appropriate conditions, in particular appropriate pH conditions, anion exchange moieties are capable of binding anions. However, they do not need to be associated with an anion. The anion exchange moieties may also form part of a compound or composition which is bound to the surface of the solid phase. Preferably, the surface is functionalized with one or more anion exchange moieties comprising one or more anion exchange groups. The term "moiety" does not include any restrictions with respect to size. The same or different anion exchange groups may be present within one moiety if the moiety comprises more than one anion exchange group. Examples of suitable anion exchange moieties include but are not limited to monoamines, diamines, polyamines, and nitrogen-containing aromatic or aliphatic heterocyclic groups as well as cyclic amines, aromatic amines and heterocyclic amines. Preferably, the anion exchange moiety comprises at least one primary, secondary and/or tertiary amino group. In preferred embodiments, the anion exchange moiety comprises or consists of a primary, secondary or tertiary amine of the formula

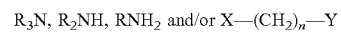

$R_3N$, $R_2NH$, $RNH_2$ and/or $X—(CH_2)_n—Y$ wherein
X is $R_2N$, RNH or $NH_2$,
Y is $R_2N$, RNH or $NH_2$,
R is independently of each other a linear, branched or cyclic alkyl, alkenyl, alkynyl or aryl substituent which may comprise one or more heteroatoms, preferably selected from O,
N, S and P, and
n is an integer in the range of from 0 to 20, preferably 0 to 18.

Hence, the anion exchange moieties comprises an anion exchange group and optionally may have more than one anion exchange group which may be the same or different from each other. An anion exchange group preferably is a chemical group which is neutral or uncharged at a high pH value and is protonated at a low pH value, thereby having a positive charge. At which pH value an anion exchange group becomes positively charged depends on its pKa value. The pKa value of the anion exchange group may lie in the range of from about 7.5 to 14, 8 to about 14, preferably from about 8.5 to about 13.5, 8.75 to 13, more preferably from 9 to 12.5, 9.25 to 12, 9.5 to 11.5 or from about 9.5 to about 11. A pKa value of at least 8, preferably at least 8.5, more preferred at least 9, most preferred at least 9.5 is advantageous, because the anion exchange moieties are positively ionisable and thus positively charged already at low to moderate pH values. The anion exchange moieties are positively ionisable at appropriate pH values thereby enabling attraction and binding of negatively charged molecules and in particular enabling attraction and binding of nucleic acids.

The amino groups may bear alkyl, alkenyl, alkynyl and/or aromatic substituents, including cyclic substituents and substituents which together with the nitrogen atom form a heterocyclic or heteroaromatic ring. The substituents preferably comprise 1 to 20 carbon atoms, more preferably 1 to 12, 1 to 8, 1 to 6, 1 to 5, 1 to 4, 1 to 3 or 1 or 2 carbon atoms. They may be linear or branched and may comprise heteroatoms such as oxygen, nitrogen, sulfur, silicon and halogen (e.g. fluorine, chlorine, bromine) atoms and may be substituted as well. Preferably, the substituents comprise not more than 4, more preferably not more than 3, not more than 2 or not more than 1 heteroatom. In one embodiment the anion exchange moiety carries 1 to 30, 1 to 25, 1 to 20, 1 to 15, 1 to 10, 2 to 8 or 2 to 6 amino groups.

Particular examples of anion exchange moieties include but are not limited to aminomethyl (AM), aminoethyl (AE), aminoalkyl, alkylaminoalkyl, dialkylaminoalkyl such as diethylaminoethyl (DEAE), N,N-diethylaminopropylt-rimethoxysilane (DEAPS), ethylendiamine, diethylentriamine, triethylentetraamine, tetraethylenpentaamine, pentaethylenhexaamine, trimethylamino (TMA), triethylaminoethyl (TEAE), linear or branched polyethylenimine (PEI), carboxylated or hydroxyalkylated polyethylenimine, jeffamine, spermine, spermidine, 3-(propylamino) propylamine, polyamidoamine (PAMAM) dendrimers, polyallylamine, polyvinylamine, N-morpholinoethyl, polylysine, and tetraazacycloalkanes. Preferred anion exchange moieties include dialkylamino groups, especially diethylamino groups or linear or branched polyethylenimine (PEI). Linear polyethyleneimines (PEIs) contain secondary amines, in contrast to branched PEIs which contain primary, secondary and tertiary amino groups.

In one embodiment, the anion exchange moieties comprises an entity selected from the group consisting of primary, secondary and tertiary mono- and poly-amines of the formula $R_1R_2R_3N$, $R_1R_2N(CH2)_nNR_3R_4$, $R_1R_2N(CH2)_nNR_3(CH2)_mNR_4R_5$, $R_1R_2N(CH2)_nNR_3(CH2)_mNR_4(CH2)_oNR_5R_6$ $R_1R_2N(CH2)_nNR_3(CH2mNR_4(CH2)_oNR_5(CH2)_pNR_6R_7$ $R_1R_2N(CH2)_nNR_3(CH2mNR_4(CH2)_oNR_5(CH2)_pNR_6(CH2)_qNR_7R_8$ $R_1R_2N(CH2)_nNR_3(CH2)_mNR_4(CH2)_oNR_5(CH2)_pNR_6(CH2)_qNR_7(CH2)_rNR_8R_9$ $R_1R_2N(CH2)_nNR_3(CH2)_mNR_4(CH2)_oNR_5(CH2)_pNR_6(CH2)_qNR_7(CH2)_rNR_8(CH2)_sNR_9R_{10}$ wherein
m, n, o, p, q, r and s independently from one each other can be 2 to 8, $R_1$, $R_2$, $R_3$, $R_4$, $R_5$, $R_6$, $R_7$, $R_8$, $R_9$ and $R_{10}$ can be identical or different and are chosen from the group H, alkyl (branched or unbranched, saturated or unsaturated, preferably comprising 1 to 10 C atoms) and aryl.

In one embodiment, the anion exchange moiety comprises N-propyl-1,3-propandiamine or pentaethylene hexamine. In certain embodiments, the anion exchange moieties are selected from spermine and spermidine.

According to the present invention the surface may comprise and can accordingly be functionalized with more than one type of anion exchange moieties. Thus, also two or more different anion exchange moieties can be present on the surface. Accordingly, it is within the scope of the present invention that the surface comprises a mixture of different anion exchange moieties. However, it is also within the scope of the present invention to predominantly or exclusively use one type of anion exchange moiety.

For functionalizing a surface with functional groups such as anion exchange moieties, several methods are feasible. The functional groups such as anion exchange moieties may be bound directly to the surface, either covalently or non-covalently, electrostatically and/or may form part of a polymer or other composition which forms a surface coating or which is provided at the surface of the solid phase. They may also be precipitated on the solid phase. According to one embodiment, the anion exchange moieties are provided in form on a coating on the solid phase.

According to one embodiment, a covalent coupling strategy is used. According to one embodiment, the solid phase comprises at its surface functional groups that are suitable for covalent attachment of the anion exchange moieties. The particle surface comprises Si—OH groups which can be used for coupling. The functional groups that are used for coupling of the anion exchange moieties may be attached directly to the solid phase or via (linear or branched) spacer or linker groups, e.g. hydrocarbons such as —$(CH_2)_n$— groups, carbohydrates, polyethylenglycols and polypropylenglycols.

According to one embodiment, functional groups such as anion exchange moieties are coupled to said surface using silanes. Examples for the modification of silica surfaces with silanes can be found in E. Plueddeman, (Silane coupling agents, second edition, Plenum Press, New York, 1991, p. 82-83). In one embodiment the silica hydroxyl groups of the silica material are reacted with alkoxy silanes. This allows the generation of a network covering the surface of the particles, since the alkoxy silanes can react with each other and also with the silanol groups on the surface. In one embodiment of the invention the particles are modified with only one silane, in another embodiment a mixture of two or more silanes is used. In a preferred embodiment of the invention two or more types of silanes are used, wherein at least one type of silane comprises a nucleic acid binding group such as e.g. a primary, secondary, tertiary or quaternary amine and at least one other type of silane is uncharged. As a result the "amino"-surface of the particle is diluted with uncharged groups which thus modify the nucleic acid binding characteristics of the particle. According to one embodiment, the silica particles are functionalised with 3-N,N-diethylaminopropyl-trialkoxysilane and 3-glycidoxypropyl-trimethoxysilane.

According to one embodiment the anion exchange moieties are tertiary amino groups, such as dialkylamino groups, preferably diethylamino groups such as diethylaminopropyl groups. They can be introduced by a silane group, i.e. via silanization. The silica surface may be derivatized with a dialkylamino silane compound such as diethylaminopropyl trimethoxysilane.

In another embodiment of the invention, functional groups are introduced by non-covalent binding of ligands possessing said functional groups. In a preferred embodiment these ligands are mono- or polyamines, more preferably spermine or spermidine.

Suitable functionalization strategies and functional groups that can be used for modifying the particle surface are also described in WO 2010072834, WO 2010072821, DE10 2008 063 001A1 and DE 10 2008 063 003 to which it is referred.

In one aspect of the invention the particles can be modified in order to harbour cation exchange groups such as e.g. carboxyl groups. In a preferred embodiment, amino-functionalised silica particles are used for this purpose. Preferably, said amino groups can react with acid anhydride to the respective carboxyalkylamides. Alternatively, polycarboxylates such as polyacrylic acid, polymethacrylic acid or polymaleic acid can react with the amino groups with the addition of an activating substance such as carbodiimides like 1-ethyl-3-(3-dimethylaminopropyl)carbodiimide (EDC) or carbonyldiimidazole. Also other functionalization strategies are feasible.

The Particles

Silica particles that are obtained with the production method of the present invention have a size of 30 µm or less, 25 µm or less, 20 µm or less, 15 µm or less, 10 µm or less, 5 µm or less or 3 µm or less. Suitable parameters and variations of the method which influence the particle size were described above. The particle size is determined based upon the diameter of the particle. Smaller particles having a median size of 5 µm or less, preferably 3 µm or less usually have a higher nucleic acid binding capacity. According to one embodiment, the obtained particles have a size selected from 100 nm to 25 µm, 250 nm to 15 µm, 500 nm to 10 µm, 750 nm to 7.5 µm, 1 µm to 5 µm and 1.5 µm to 2.5 µm. In one embodiment of the invention the particles have a size of 50 nm to 25 µm, preferably of 100 nm to 10 µm, more preferably of 100 nm to 5 µm and most preferably of 250 nm to 3 µm. The method of the invention allows to obtain particles having a relatively narrow particle size distribution. According to one embodiment, the particle size distribution is such that about 70%, preferably 80% or 90% of the produced particles are within a 10 µm range about the median particle size, within a 7.5 µm range about the median particle size, more preferred within an 5 µm range about the median particle size or within a 2.5 µm range about the median particle size.

As described above, the particles obtained by the method according to the present invention are preferably formed by agglomerated $SiO_2$ coated core particles. Thereby, porous silica particles are provided. These porous silica particles may have macropores that are formed between the agglomerated $SiO_2$ coated core particles in the interstices. Furthermore, preferably, the surface also comprises micropores. The porous particles of the invention have a large total surface area which can be measured by the nitrogen Brunaur Emmet Teller (BET) method. A IUPAC definition of pore sizes and information regarding the characterization of porous materials is given e.g. in Pure & Appl. Chem., Vol. 66, No. 8, pp. 1739-1758, 1994.

The method according to the invention leads to particles wherein the core particles are essentially completely surrounded and thus encapsulated by the $SiO_2$ coating. This prevents an exposure of the core particles to the surrounding medium. In case of particles with an iron oxide core, this advantageously prevents the release of substantial amounts of iron oxide from the particle.

In one embodiment of the invention, the magnetic silica particles prepared by the method of the invention have a composition regarding the comprised $SiO_2$ and iron oxide that is about 15 to 75% (by weight) iron oxide and about 25% to 85% (by weight) $SiO_2$, preferably 20 to 50% (by weight) iron oxide and about 50 to 80% (by weight) $SiO_2$, more preferred 25 to 50% (by weight) iron oxide and about 50 to 75% (by weight) $SiO_2$. According to one embodiment, $Fe_3O_4$ is used as iron oxide. The concentration of iron oxide core particles and silicate in the reaction composition is adjusted to achieve a respective composition in the obtained magnetic silica particles. The described ratios for iron oxide/$SiO_2$ are favourable, as they achieve a balance between sufficiently strong magnetic properties of the obtained particles and the prevention of an (unwanted) agglomeration of the magnetic particles. The described ratios also generally apply to the ratio core particles/$SiO_2$. Details regarding the core particles are described above and it is referred to the above disclosure which also applies here.

As discussed above, the particles may also comprise other compounds e.g. oxides of other metals. According to one embodiment, the $SiO_2$ coating comprises at least 80% by weight (dry basis) $SiO_2$, preferably at least 90% by weight $SiO_2$, more preferred 95% to 100% by weight $SiO_2$. E.g. the $SiO_2$ coating may contain alkali metal ions associated with the formation of the coating, however, the coating preferably contains less than about 1.5% by weight, more preferred less than about 1% by weight, more preferred less than about 0.5% by weight, most preferred less than 0.2% by weight of alkali metal measured as alkali metal oxide.

In a preferred embodiment, the magnetic silica particles prepared by the method of the invention bind at least 1 µg nucleic acids per mg particles, at least 2 µg nucleic acid molecules per mg particles, at least 5 µg nucleic acid molecules per mg particles, at least 7.5 µg nucleic acid molecules per mg particles, at least 10 µg nucleic acid molecules per mg particles, at least 12.5 µg nucleic acid molecules per mg particles, at least 15 µg nucleic acid molecules per mg particles, at least 17.5 µg nucleic acid molecules per mg particles and more preferably at least 20 µg nucleic acid molecules per mg particles. As is shown by the examples, silica particles produced according to the teachings of the present invention achieve high binding capacities which are even higher than those of prior art silica particles. According to one embodiment, the nucleic acid binding capacity is determined using the method described in example 6. This method can also be used for testing non-magnetic particles. When assaying non-magnetic silica particles, the silica particles can be separated by way of sedimentation or centrifugation.

According to one embodiment, the yield of nucleic acids isolated using the silica particles of the invention is at least 70% and preferably at least 80%.

Therefore, according to a second aspect, the present disclosure provides porous silica particles having a size of 30 µm or less, which are formed by agglomerated $SiO_2$ coated core particles, wherein the core particles are essentially encapsulated by the $SiO_2$ coating and wherein the silica particles have a composition regarding the comprised $SiO_2$ and core particles that is 15 to 75% (by weight) core particles and 25% to 85% (by weight) $SiO_2$, and wherein the silica particles are capable of binding at least 12.5 µg nucleic acid molecules per mg particles. Details regarding the size of the particles (determined based on the diameter), the core particles, the nucleic acid binding capacity and ways to determine it, and the composition of the silica particles regarding the comprised $SiO_2$ and core particles are described above and it is referred to the above disclosure which also applies here. Non-limiting embodiments are again briefly described in the following.

According to one embodiment, the silica particles are capable of binding at least 12.5 µg nucleic acid molecules per mg particles, at least 15 µg nucleic acid molecules per mg particles or at least 17.5 µg nucleic acid molecules per mg particles. As is shown by the examples, the silica particles of the present invention are even capable of binding at least 20 µg nucleic acid molecules per mg particles. This extraordinary high nucleic acid binding capacity is an important advantage over prior art silica particles. As described above, according to one embodiment, the nucleic acid binding capacity of the particles is determined as described in example 6.

The porous silica particles may comprise macropores. According to one embodiment, the surface of the particles additionally comprises micropores. Micro- and macropores can be determined as described by IUPAC (see above). According to one embodiment, the particles have a size of 25 µm or less, 20 µm or less, 15 µm or less, 10 µm or less, 5 µm or less or 3 µm or less. Suitable size ranges are also described above. The silica particles may have a size that lies within the range of 50 nm to 25 µm, 100 nm to 10 µm, 100 nm to 5 µm or 250 nm to 3 µm.

According to one embodiment, the porous silica particles have a composition regarding the comprised $SiO_2$ and core particles that is 20 to 50% (by weight) core particles and about 50 to 80% (by weight) $SiO_2$, preferably 25 to 50% (by weight) core particles and about 50 to 75% (by weight) $SiO_2$ (see also above). According to one embodiment, the silica particles have an unmodified silica surface.

According to one embodiment, the contained core particles have magnetic properties. E.g. the core particles may have superparamagnetic, paramagnetic, ferromagnetic or ferrimagnetic properties. Suitable materials were described in detail above. According to one embodiment, the particles comprise iron oxide, preferably magnetite and/or maghemite as core particles. According to one embodiment, the core particles, which preferably are magnetic, have a diameter that lies in a range selected from 8 to 150 nm, 10 to 100 nm and 10 nm to 60 nm.

As described, the silica particles according to the second aspect are obtainable by the method according to the first aspect. Details with respect to said method according to the first aspect are described above, and it is referred to the above disclosure. The particles are due to their high nucleic acid binding capacity preferably used for isolating nucleic acids.

Use of the Particles

According to a third aspect, the present disclosure pertains to the use of silica particles produced according to the method according to the first aspect or the use of silica particles according to the second aspect, for isolating biomolecules, in particular for isolating nucleic acids from various samples.

The particles produced with the method according to the present invention as well as the particles according to the second aspect can be used basically in all fields in particular all fields of life science, including but not limited to isolation of biomolecules, biological materials such as cells or cell organelles, analytical, forensic, diagnostic or medical applications.

The silica particles obtained by the method according to the present invention have a high capacity to bind biomolecules such nucleic acids, thereby making the particles of this invention especially useful for isolating or separating biomolecules such as nucleic acid molecules from various samples and mixtures. The biomolecule to be isolated may be selected from the group consisting of nucleic acids, proteins, polypeptides, peptides, carbohydrates, lipids, and combinations thereof. In particular, the particles produced according to the present invention are suitable for isolating nucleic acids.

Subsequently, the use of the particles produced by the method of the invention for isolating nucleic acids from samples will be described in further detail. The term "sample" in this respect is used in a broad sense and is intended to include a variety of sources that contain nucleic acids. The sample may be a biological sample but the term also includes other, e.g. artificial samples which comprise nucleic acids such as in vitro reaction mixtures that contain nucleic acids, such as polymerase chain reactions (PCR), nucleic acid sequencing reactions, restriction endonuclease or other nuclease digestion reactions, nucleic acid hybridization assay mixture, in vitro transcription and/or translation assay mixtures and amplification reactions. Preferably, the sample is a biological sample. Exemplary biological samples include, but are not limited to, tissues, including but not limited to, liver, spleen, kidney, lung, intestine, brain, heart, muscle, fat, pancreas, cells, cell cultures, body fluids in general; whole blood; serum; plasma; red blood cells; white blood cells; buffy coat, tumor cells, fetal cells, host and graft cells; swabs, including but not limited to buccal swabs, throat swabs, vaginal swabs, urethral swabs, cervical swabs, throat swabs, rectal swabs, lesion swabs, abscess swabs, nasopharyngeal swabs, and the like; urine; sputum; saliva; semen; lymphatic fluid; liquor; amniotic fluid; cerebrospinal fluid; peritoneal effusions; pleural effusions; fluid from cysts; synovial fluid; vitreous humor; aqueous humor; bursa fluid; eye washes; eye aspirates; pulmonary lavage; lung aspirates; bone marrow aspirates, cells in suspension, as well as lysates, extracts, or materials obtained from any cells and microorganisms and viruses that may be present on or in a sample and the like. Materials obtained from clinical or forensic settings that contain nucleic acids are also within the intended meaning of the term biological sample. Furthermore, the skilled artisan will appreciate that lysates, extracts, or materials or portions thereof obtained from any of the above exemplary samples are also within the scope of the term sample. Preferably, the sample is a biological sample derived from a human, animal, plant, bacteria or fungi. It may be of prokaryotic or eukaryotic origin. In particular, the term "sample" refers to a nucleic acid containing sample which also comprises cells. Preferably, the sample is selected from the group consisting of cells, tissue, body fluids such as for example blood, blood products such as buffy coat, plasma and serum, urine, liquor, sputum, stool, CSF and sperm, epithelial swabs, biopsies, bone marrow samples and diverse tissue samples. The biological sample may be preserved and e.g. may be contained in preservative medium. E.g. the sample from which the nucleic acids are to be isolated may have been stored in a preservative, including but not limited to paraffin-embedded tissue samples and cellular and tissue or cell samples stored in a liquid-based cytology medium such as SUREPATH® or PRESERVCYT®. Also other biomolecules such as e.g. proteins can be isolated from the samples mentioned above which comprise the respective biomolecule of interest.

The term "nucleic acid" or "nucleic acids" as used herein, in particular refers to a polymer comprising ribonucleosides and/or deoxyribonucleosides that are covalently bonded, typically by phosphodiester linkages between subunits, but in some cases by phosphorothioates, methylphosphonates, and the like. DNA includes, but is not limited to all types of DNA, e.g. gDNA; circular DNA, plasmid DNA and circulating DNA. RNA includes but is not limited to hnRNA; mRNA; extracellular RNA, noncoding RNA (ncRNA), including but not limited to rRNA, tRNA, lncRNA (long non coding RNA), lincRNA (long intergenic non coding RNA), miRNA (micro RNA), siRNA (small interfering RNA), snoRNA (small nucleolar RNA), snRNA (small nuclear RNA) and stRNA (small temporal RNA), piRNA (piwi interacting RNA), tiRNA (transcription initiation RNA), PASR (promoter associated RNA), CUT (cryptic unstable transcripts). The nucleic acids can include double-stranded and/or single-stranded nucleic acids; they can be single-stranded or double-stranded DNA, RNA or DNA-RNA hybrids. The nucleic acids can comprise modified nucleotides. As used herein, a modified nucleotide is a nucleotide that has been structurally altered so that it differs from a naturally-occurring nucleotide. Such modified nucleotides include nucleotides which contains a modified sugar moiety, a modified phosphate moiety and/or a modified nucleobase. Also included are peptide nucleic acids (PNA), locked nucleic acids (LNA), ribozymes, aptamers, spiegelmers, and chemically synthesized nucleic acid molecules.

Particularly preferred is the use of magnetic particles produced according to the present invention for isolating biomolecules such as nucleic acids or other targets such as cells. To enable the specific capture of a target, the silica particles can be functionalized with appropriate chemical functionalities or ligands (see above) which allow a respective specific capture. The magnetic property of the magnetic particles permits the particles to be easily and rapidly collected from a sample or mixture by applying an external magnetic field using any of a variety of magnetic collection systems available in the art.

Suitable methods for isolating biomolecules such as nucleic acids using silica particles are well-known to the skilled person and thus, do not need any detailed description here. Suitable methods for binding nucleic acids to silica particles, and also for selectively binding specific types of nucleic acids are e.g. described in EP 0 389 063, EP 0 880 537 and WO 9521849 and WO 0171732. Generally, the particles of the present invention can be used in any nucleic acid isolation method that can be performed with silica particles. Non-limiting examples are also described below.

According to one aspect of the present invention, a method for isolating nucleic acids from a sample is provided comprising the following steps:
  binding nucleic acids contained in the sample under appropriate conditions to the silica particles produced according to the method according to the first aspect of the present invention;
  separating the particles with the bound nucleic acids from unbound components;
  optionally washing the bound nucleic acids;
  optionally eluting the bound nucleic acids.

If the sample does not contain the nucleic acids of interest in an accessible form, the nucleic acids can first be released, e.g. by lysing the sample. Different methods can be used in order to achieve the lysis of the sample and suitable lysis methods are well-known in the prior art. The term "lysis" as used herein refers to the disruption, degradation and/or digestion of a sample or portion or fraction thereof. In a respective lysis step, biomolecules such as in particular nucleic acids can be released from cells or can be freed from other sample additives such as e.g. proteins. Herein, it is referred to a respective step to disrupt, degrade and/or digest a sample generally as lysis step, irrespective of whether biomolecules such as in particular nucleic acids are released from cells or whether the lysis is performed in order to release biomolecules such as nucleic acids e.g. from proteins or other substances comprised in the sample. Hence, the sample may comprise cells or may comprise no or only minor amounts of cells as is e.g. the case with blood plasma. Preferably, for lysis the sample is contacted with one or more lysing agents. Nucleic acids such as RNA can be protected from degradation by nucleases during lysis. The chosen lysis conditions may also vary depending on the type of sample to be processed. Generally, the lysis procedure may include but it is not limited to mechanical, chemical, physical and/or enzymatic actions on the sample. Examples include but are not limited to grinding the sample in a bead mill or in the presence of glass beads, homogenising the sample, the application of ultrasound, heating, the addition of one or more detergents and/or the addition of protein degrading compounds, such as for example protein degrading enzymes or salts. Furthermore, reducing agents such as beta-mercaptoethanol or DTT can be added for lysis to assist denaturation of e.g. nucleases. For isolating nucleic acids using silica particles from biological samples it is preferred to use as least one chaotropic agent, preferably at least one chaotropic salt, during lysis of the sample. Suitable chaotropic agents and in particular chaotropic salts are well known and are also described subsequently. Furthermore, during lysis, also other additives can be added such as chelating agents, nuclease inhibitors, in particular RNase inhibitors or DNase inhibitors (in particular if the parallel isolation of RNA and DNA is intended), detergents and the like. Respective additives that can be used to support the lysis of the sample and to protect the released nucleic acids, in particular the released RNA, are well-known in the prior art and thus, do not need to be described in detail herein.

The nucleic acids may be bound to the silica particles produced by the method of the invention in the presence of salts that promote binding of the nucleic acid to the particles. Under these conditions, nucleic acids also bind to the unmodified silica surface. Preferably, one or more chaotropic agents are present during binding, in particular chaotropic salts. The respective chaotropic salts can be added for lysis and/or to establish suitable binding conditions in the binding mixture. Examples of chaotropic agents include but are not limited to sodium perchlorate, potassium perchlorate, ammonium perchlorate or other perchlorate containing chaotropic salts, guanidinium hydrochloride, guanidinium isothiocyanate, sodium isothiocyanate, guanidinium thiocyanate, potassium thiocyanate or other guanidinium containing chaotropic salts, thiocyanate containing chaotropic salts and/or isothiocyanate containing chaotropic salts, potassium iodide, potassium iodide or sodium iodide or other iodide containing chaotropic salts and urea. The chaotropic agent may be used for binding at a concentration that is, preferably, in the range of 1 to 8 M; more preferably, in the range of 1.5 to 5 M; and, most preferably, in the range of 2 to 4 M. However, also other salts, in particular non-chaotropic salts can be used in order to promote binding of the nucleic acids to the silica surface. Respective methods wherein nucleic acids are bound in the absence of chaotropic agents to silica surface are well-known in the prior art and thus do not need any further description here.

Furthermore, an alcohol such as a C1-C5 aliphatic alcohol, such as methanol, ethanol, n-propanol, isopropanol, n-butanol, tert-butanol, n-pentanol, or combinations thereof can be used to promote binding of the nucleic acids to the silica surface. The use of alcohol is particularly preferred when isolating RNA. The alcohol may be comprised in the binding mixture in a concentration of 1 to 85% (v/v), preferably 15% to 75% (v/v), more preferred 20% to 70% (v/v). Furthermore, the binding mixture may comprise a detergent. The concentrations of salts and/or alcohols may be adjusted so that nucleic acids are bound selectively to the silica particles. Furthermore, it is possible to separate nucleic acids of different lengths from each other by adjusting the concentrations of chaotropic salts and/or alcohols.

The bound nucleic acids are then separated from unbound components. Separation can be achieved by any means such as filtration, sedimentation or centrifugation. The supernatant can then be discarded. If magnetic silica particles are used, separation can be achieved by the aid of a magnetic field. Suitable methods for processing magnetic particles are well-known to the skilled person and thus, do not need any further description herein.

If desired, one or more washing steps can be performed. Suitable wash solutions are known in the prior art. The wash solution may contain alcohols, other highly volatile organic solvents such as acetone, and even one or more chaotropic agents. Also water may be used for washing.

If it is appropriate for further utilization of the nucleic acid molecules, the nucleic acid molecules may be eluted from the particles. For elution, water, aqueous solutions of low salt concentrations, Tris-buffers and other suitable elution solutions can be used. However, for several applications, it is not necessary to elute the nucleic acids. E.g. the silica particles carrying the bound nucleic acids may also be directly subjected to an analytical reaction, such as an hybridization assay or an amplification reaction.

In another aspect of the invention the particles that are modified with an anion exchanger are used for the purification of nucleic acids, whereby the nucleic acids are bound at a first pH value, optionally washed with deionised water or a low-salt-buffer, and eluted at a second pH value which is higher than the first pH value. Therefore, respectively functionalized silica particles produced by the method of the present invention can be used for isolating nucleic acids applying a charge switch based isolation approach. According to one embodiment, particles which are coated with a mixture of 3-N,N-diethylaminopropyl-trialkoxysilane and 3-glycidoxypropyl-trimethoxysilane can bind DNA and RNA at a pH value of 6, the impurities can be removed by washing with deionised water and the bound nucleic acids are eluted by using an elution buffer with a pH value of 8.0 or above. Suitable nucleic acid isolation methods that involve the use of respectively modified particles are described in WO 2010072834, WO 2010072821, DE10 2008 063 001A1 and DE 10 2008 063 003.

In a further aspect of the invention, the carboxylate-functionalised particles can be used for a polyethylene glycol (PEG)-induced precipitation as disclosed in e.g. U.S. Pat. No. 5,705,628. This method is based on the principle that nucleic acids precipitate in the presence of PEG and bind to hydrophilic surfaces. For this purpose also unmodified particles with a silica surface can be used as is shown in the examples.

The silica particles described herein have a relatively high binding capacity for various molecules, and especially nucleic acids, such that the particles are useful in isolating or separating molecules from a mixture in useful yields. The particles may be used in both analytical as well as preparative scale procedures. Particles having a particular porosity, binding capacity, and binding specificity can be obtained by selectively changing various synthetic reaction parameters according to the invention.

Numeric ranges described herein are inclusive of the numbers defining the range. The headings provided herein are not limitations of the various aspects or embodiments of this invention which can be read by reference to the specification as a whole. The term "solution" as used herein, in particular refers to a liquid composition, preferably an aqueous composition. It may be a homogenous mixture of only one phase but it is also within the scope of the present invention that a solution that is used according to the present invention comprises solid components such as e.g. precipitates. According to one embodiment, subject matter described herein as comprising certain steps in the case of methods or as comprising certain ingredients in the case of compositions, solutions and/or buffers refers to subject matter consisting of the respective steps or ingredients. It is preferred to select and combine preferred embodiments described herein and the specific subject-matter arising from a respective combination of preferred embodiments also belongs to the present disclosure.

This invention is not limited by the exemplary methods and materials disclosed herein.

EXAMPLES

Example 1: One-Step-Preparation of Magnetic Silica Particles 14 liters of process water are placed in a 20 liter double-wall reactor provided with a paddle mixer, thoroughly flushed with nitrogen and suspended with 228 g KOH under stirring at 500 rpm. By continuously stirring at 500 rpm an argon flushed mixture containing 2×109.5 g iron(III)chloride hexahydrate (Sigma Aldrich, Art. no. 44944) and 2×40.32 g iron(II)chloride tetrahydrate (Sigma Aldrich, Art. no. 44939) in a volume of 2×600 ml deionised water are added and further stirred for 2 hours at 150 rpm under nitrogen supply. Afterwards, 15 g sodium citrate monohydrate (Sigma Aldrich, Art. no. 71402) and 15 ml potassium silicate solution (KaSil, Cognis AG, today BASF: Art. no. 1700) are added and stirred for 15 minutes at 250 rpm. Then, 161.2 g potassium hydroxide (Sigma Aldrich, Art. no. 60368), 300 ml potassium silicate solution and 405 ml formamide (Sigma Aldrich, Art. no. 47670) are given to the suspension, and after stopping the nitrogen supply, the suspension is stirred over night at 250 rpm.

After 17 hours the total reaction is further processed. The pH value is analysed and the reaction mixture is processed using 8 centrifuge buckets with a volume capacity of 2 liters. 1500 ml of the suspension are filled into each of the centrifuge buckets. The filled buckets are agitated and after prolonged magnetisation the supernatant is decanted. The bead suspension is washed 5 times with deionised water. Then, the centrifuge buckets are left for sonication in an ultrasound bath for 2 minutes. After 2 additional washing steps with deionized water, the magnetic particles are pooled in one or more Nalgene bottles for storage under deionized water.

During the reaction the pH value has dropped from 14 to 10.74. The so prepared particles have a mean size of 20 µm. Smaller particles e.g. having a median size that lies in a range of 5 to 10 μm can be obtained by reducing the silicate concentration and/or increasing the steering speed.

Example 2: Two-Step-Preparation of Magnetic Silica Particles 1 liter of process water is placed in a dissolver reactor provided with a propeller mixer (VMA Getzmann, Reichshof-Bergneustadt, Germany) and 5 g (related to the $Fe_3O_4$ weight) of citrate-stabilised magnetite (e.g. Alfa Aesar, Art. no. 44665) are slowly suspended at 2000 rpm into the solution. While continuously stirring at 2000 rpm, 1 g citric acid monohydrate (Sigma-Aldrich, Art no. 27490) and 1 ml potassium silicate solution are added and the suspension is stirred for further 15 minutes. Afterwards, 13.75 g potassium hydroxide, 25 g potassium silicate solution (KaSil, Cognis AG, today BASF: Art. no. 1700) and 30 g formamide are given to the suspension which is then stirred overnight at 2000 rpm. After 16 and 17 hours 25 ml of the suspension are removed, and the complete reaction mixture is processed after 18 hours. For this purpose, the pH value is determined, 1 liter of process water is added to the bead suspension and further stirred for 10 min at 2000 rpm. Further processing is performed in centrifuge buckets with a volume capacity of 2 liters. The centrifuge buckets are loaded with 1000 ml of suspension, agitated, and after prolonged magnetisation the supernatant is decanted. The magnetic precipitate is pooled in a Nalgene bottle, washed three times with deionised water, two times with technical-grade ethanol and once more with deionised water. The bead suspension is stored under deionised water.

During the reaction the pH value has dropped from 14 to 10.64. The so prepared particles have a mean size of 2.5 μm (Coulter LS, in volume terms).

Example 3: Modification of the Magnetic Silica Particles with an Anion Exchanger Surface (Uniform Silanisation)

500 mg of the bead suspension comprising the silica particles to be modified is removed and pipetted into a 50 ml Falcon tube, washed for four times with 10 ml of deionised water, and the separation of the supernatants is performed after magnetisation for 3 minutes. Then, 5.75 ml deionised water, 750 μl QSP1-buffer (containing 100 mM sodium acetate, pH 5.6) and 30 μl diethylaminopropyl-trimethoxysilane are added. The mixture is thoroughly vortexed and incubated for four hours at a temperature of 95° C. in an Eppendorf-shaker at 1000 rpm. Subsequently, the beads are washed three times with 10 ml deionised water, two times with 10 ml absolute ethanol, and finally three times with 10 ml deionised water. The washing steps are performed by briefly vortexing the beads and removal of the wash solution after about 5 minutes of magnetic separation. The beads are resuspended afterwards in 2 ml MES buffer (50 mM 2-(N-morpholino)ethanesulfonic acid, pH 6.1).

Example 4: Modification of the Magnetic Silica Particles with an Anion Exchanger Surface (Mixed Silanisation)

500 mg of the bead suspension comprising the silica particles to be modified is removed and pipetted into a 50 ml Falcon tube, washed for four times with 10 ml deionised water, and the separation of the supernatants is performed after magnetisation for 3 minutes. Afterwards, 5.75 ml deionised water, 750 μl 1M sodium acetate, pH 5.5, 7.1 μl diethylaminopropyl-trimethoxysilane and 18.75 μl 3-glycidoxypropyl-trimethoxysilane are added. The mixture is thoroughly vortexed and incubated for four hours at a temperature of 95° C. in an Eppendorf-shaker at 1000 rpm. Subsequently, the beads are washed three times with 10 ml deionised water, two times with 10 ml absolute ethanol and finally three times with 10 ml deionised water. The washing steps are performed by briefly vortexing the beads and removal of the wash solution after about 5 minutes of magnetic separation. The beads are resuspended afterwards in 2 ml MES buffer (50 mM, pH 6.1).

Example 5: Modification of the Magnetic Silica Particles with a Polycarboxylate Surface 500 mg of the bead suspension comprising the silica particles to be modified is pipetted into a 50 ml Falcon tube, washed for four times with 10 ml deionised water, and the supernatant is removed after magnetic separation. Afterwards, 5.75 ml deionised water, 750 μl 1M sodium acetate, pH 5.5, 50 μl 3-aminopropyl-triethoxysilane (APTES) are added. The mixture is thoroughly vortexed and incubated for four hours at a temperature of 95° C. in an Eppendorf-shaker at 1000 rpm. Subsequently, the supernatant is removed after magnetic separation, and the beads are washed three times with 10 mL deionised water, two times with absolute ethanol and finally three times with deionised water. The washing steps are performed by vortexing the beads for a short time and removal of the wash solution after magnetic separation. By vortexing the beads are resuspended in 20 ml polyacrylic acid buffer (containing 1 g/100 ml polyacrylic acid, pH 7.5) and 250 mg of 1-Ethyl-3-(3-dimethylaminopropyl)carbodiimide (EDC) is added. The suspension is vortexed, shortly devolatilised by ultrasound, and incubated for 60 minutes at room temperature. Finally, the suspension is washed two times with 10 mM Tris, pH 8.5 and three times with deionised water. The reaction product is stored in MES buffer (50 mM, pH 6.1).

Example 6: Use of the Magnetic Silica Particles for Purification of Nucleic Acids with a Chaotropic Binding Buffer 1 mg magnetic particles prepared according to example 2 are added to 100 μl of a buffer containing 5 M guanidinium hydrochloride, 20 mM sodium acetate, and 30% isopropanol; pH 5.0. Then, 2 to 20 μg of the plasmid pUC21 are added. The reaction mixture is shaken at room temperature for 10 min at 1000 rpm in an Eppendorf shaker, and the supernatant is removed after magnetic separation. Afterwards, the beads are washed two times with 100 μl of washing buffer containing 80% ethanol, 10 mM Tris, pH 7.5. The washing steps are performed by shaking the beads for 10 minutes at 1000 rpm and removal of the washing buffer after magnetic separation. After the last washing step, while remaining in the magnetic separator, the reaction tubes are turned upside down for 10 minutes in order to remove residual ethanol. The elution is performed by adding 100 μl of elution buffer (10 mM Tris, pH 8.5) and shaking the suspension for 10 minutes at 1000 rpm. After magnetic separation the eluate is removed and the DNA content of the eluate is determined by photometric and gelelectrophoretic analysis.

Results:

The gelelectrophoretic analysis as shown in FIG. 1 reveals an amount-dependent isolation of the DNA without signs of degradation. The gelelectrophoretic analysis and the photometric analysis (see FIG. 2) demonstrate that 1 mg silica beads prepared according to the teachings of the present invention allow a purification of at least 20 µg of DNA.

Example 7: Use of the Magnetic Silica Particles Modified with an Anion Exchanger for Purification of Nucleic Acids The particles NB-12 to NB-15 were obtained from the same synthesis (see Example 2), however, were obtained after 16 h (NB-12), 17 h (NB-13) and 18 h (NB-15) reaction time. 0.5 mg magnetic particles (prepared according to Example 2 and modified according to Example 4) are added to 100 µl MES buffer containing 25 mM MES, pH 6.0. Afterwards, 5, 10 or 15 µg of the plasmid pUC21 is added. The mixture is shaken at room temperature for 10 min at 1000 rpm in an Eppendorf shaker, and the supernatant is removed after magnetic separation. Then, the beads are washed two times with 100 µl of deionised water. The washing steps are performed by shaking the beads for 10 minutes at 1000 rpm and removal of the wash solution after magnetic separation. The elution is performed by adding 100 µl of elution buffer (100 mM Tris, 100 mM NaCl, pH 8.5) and shaking the suspension for 10 minutes at 1000 rpm. After magnetic separation the eluate is removed and the DNA content of the eluate is determined by photometric and gelelectrophoretic analysis.
Results:
The gelelectrophoretic analysis is shown in FIG. 3. Here, the supernatant (SN) obtained after binding the DNA to the beads was analysed. As can be seen, most of the DNA was efficiently bound to the beads under the used binding conditions. Furthermore, the eluates (E) were analysed. The results demonstrate that 0.5 mg of the beads allowed an efficient purification of 5 to 15 µg of plasmid DNA.

Example 8: Use of the Unmodified Magnetic Silica Particles in Comparison with Polycarboxylate Modified Magnetic Silica Particles for Purification of Nucleic Acids with Polyethylene Glycol 1 mg of the magnetic particles (prepared according to Example 1, either unmodified (UNM) or modified with carboxyl groups according to Example 5 (MC)) is suspended in 100 µl of a binding buffer containing 20% PEG 600, 1 M NaCl, 100 mM glycine, pH 4.0. Afterwards, 2 µg of the plasmid pUC21 in a buffer containing 10 mM Tris, pH 8.5 is added. The reaction mixture is shaken at room temperature for 10 min at 1000 rpm in an Eppendorf shaker, and the supernatant is removed after magnetic separation. Afterwards, the beads are washed two times with 100 µl of a washing buffer containing 80% ethanol, 10 mM Tris, pH 7.5. The washing steps are performed by shaking the beads for 10 minutes at 1000 rpm and removal of the wash solution after magnetic separation. The elution is performed by adding 100 µl of elution buffer (10 mM Tris, pH 8.5) and shaking the suspension for 10 minutes at 1000 rpm. After magnetic separation the eluate is removed and a second elution is performed as described above by using 100 µl of an elution buffer containing 50 mM Tris, 50 mM NaCl, pH 8.5 and the DNA content of the eluate was determined by photometric and gelelectrophoretic analysis.
Results:
The gelelectrophoretic analysis (see FIG. 4) and the photometric analysis (see Table 1) demonstrate that both, the unmodified silica particles (UNM) as well the polycarboxylate modified silica particles (MC) of the invention can be used for purification of nucleic acids. Nucleic acids are bound to the particle surface in presence of PEG, optionally washed and eluted with water or a low salt buffer.

TABLE 1

Photometric quantification of plasmid DNA (2 to 20 µg pUC21) purified with unmodified magnetic silica particles vs. carboxylated silica particles

| Particles | ng/µL | 260/280 | MW |
|---|---|---|---|
| Control 2 µg/100 µL | 22.1 | 1.71 | 22.1 |
| Silica Beads (MC) | 24.9 | 1.61 | 19.8 |
| " | 17.5 | 1.52 | |
| " | 19.6 | 1.57 | |
| " | 17.1 | 1.53 | |
| Silica Beads (UNM) | 14.3 | 1.49 | 14.0 |
| " | 13.2 | 1.47 | |
| " | 14.0 | 1.50 | |
| " | 14.5 | 1.43 | |

Example 9: Use of Different Magnetic Silica Particles for the Purification of Nucleic Acids Using a Chaotropic Binding Buffer The nucleic acid isolation performance of two commercial available magnetic silica particles (Mag G beads (QIAGEN), prepared according to WO 0171732; Mag B beads, prepared according to US 2006/188876) was compared with magnetic silica particles prepared according to the present invention (see Example 2). 2 to 20 µg plasmid DNA were used as input DNA. The nucleic acid isolation was performed as described in example 6. The results are shown in table 2.

TABLE 2

Photometric quantification of plasmid DNA (2 to 20 µg pUC21) purified with different unmodified magnetic silica particles

| pUC 21 | Control | Mag B beads | Mag G beads | Invention |
|---|---|---|---|---|
| 2 µg | 24.75 | 8.825 | 25.9 | 43.45 |
| 4 µg | 45.2 | 12.675 | 46.675 | 54.725 |
| 6 µg | 66.55 | 22.825 | 70.75 | 64.225 |
| 8 µg | 98 | 28.3 | 84.675 | 88.65 |
| 10 µg | 136.75 | 28.3 | 89.6 | 200.125 |
| 12 µg | 104.75 | 31.425 | 98.225 | 145.35 |
| 14 µg | 134.6 | 33.375 | 99.95 | 153.35 |
| 16 µg | 131.5 | 36.4 | 109.3 | 162.15 |
| 18 µg | 160.55 | 36.375 | 109.45 | 233.225 |
| 20 µg | 160.15 | 36.25 | 116.2 | 179.475 |

As can be seen, the magnetic silica particles prepared according to the present invention showed superior isolation properties compared to the commercially available Mag B beads. Furthermore, the magnetic silica particles according to the present invention showed equal or even superior performance compared to the commercially available Mag G beads, which are widely used for nucleic acid isolation. A decisive advantage of the magnetic silica particles prepared according to the present invention compared to the Mag G beads is the reduction of the production costs. The production costs are reduced by 13 to 14 when using the method according to the present invention. Furthermore, in contrast to other prior art methods, the method of the present disclosure is not based on spray-drying.

The invention claimed is:
1. A method for producing porous particles having a $SiO_2$ containing surface comprising:
   a) providing an aqueous reaction composition comprising
      i) core particles,
      ii) an added base,
      iii) a silicate salt, and
      iv) a pH modulator
      wherein the pH value of the reaction composition is above the gelation pH value of the silica salt;
   b) agitating said reaction composition, wherein the pH modulator is an organic compound that reacts in the alkaline milieu of the reaction composition, thereby decreasing the pH value of the reaction composition over time and wherein due to said decrease of the pH value of the reaction composition, $SiO_2$ is deposited onto the core particles, whereby porous particles are formed which have a diameter of 30 µm or less and are capable of binding at least 20 µg nucleic acid molecules per mg, particles; and
   c) obtaining the porous particles.
2. The method according to claim 1, wherein the reaction composition comprises the silicate salt in a concentration of less than 1 mol/l.
3. The method according to claim 1, having one or more of the following features:
   i) the initial pH value of the reaction composition is pH 12.5 or above;
   ii) the initial pH value of the reaction composition lies between 11 and 15;
   iii) the decreased pH value adjusted by the activity of the pH modulator is pH 12 or less; and/or
   iv) the decreased pH value adjusted by the activity of the one or more pH modulator lies in a range of 9 to 12.
4. The method according to claim 1, wherein the reaction composition comprises the silicate salt in a concentration of less than 1 mol/l, wherein the initial pH value is at 12.5 or above, and wherein after the particle formation is completed, the porous particles are collected from the reaction composition.
5. The method according to claim 1, wherein an alkali hydroxide is used as base.
6. The method according to claim 1, having one or more of the following characteristics:
   i) the obtained particles are formed by agglomerated $SiO_2$ coated core particles; and/or
   ii) particles are formed which have a median diameter from 100 nm to 25 µm.
7. The method according to claim 1, wherein the core particles have one or more of the following characteristics:
   i) the core particles have magnetic properties;
   ii) the core particles have superparamagnetic, paramagnetic, ferromagnetic or ferrimagnetic properties;
   iii) the core particles comprise iron oxide;
   iv) the core particles have a diameter that lies in a range from 8 to 150 nm and/or
   v) the core particles are hollow.
8. The method according to claim 7, wherein the iron oxide core particles are stabilised, and wherein optionally, the core particles are contacted with alkali silica prior to step a) in order to facilitate the subsequent deposition of silica in step b).
9. The method according to claim 1, having one or more of the following characteristics:
   i) the pH modulator is hydrolysed at the initial pH value of the reaction composition, wherein the hydrolysis of the pH modulator continuously decreases the pH value of the reaction composition below the gelation pH of the silicate;
   ii) the pH modulator comprised in the reaction composition reduces the initial pH value by at least 1 pH unit upon hydrolysis and/or activation of the pH modulator;
   ii) the pH modulator is an organic compound comprising an ester, an amide, an aldehyde or a polyoxymethylene group;
   iii) the pH modulator is selected from the group consisting of formaldehyde, paraformaldehyde, formamide, glyoxal, methyl formate, methyl acetate, ethyl formate, ethyl acetate, ammonia, and mixtures thereof;
   iv) the pH modulator is formamide; and/or
   v) the pH modulator is comprised in the reaction composition in a concentration of 0.1 to 2 mol/l.
10. The method according to claim 1, wherein the pH value of the reaction composition is only reduced by the activity of the pH modulator.
11. The method according to claim 1, having one or more of the following characteristics:
    i) alkali silicate is used as silicate salt;
    ii) potassium silicate of the formula $K_2O \cdot nSiO_2$ is used as silicate salt, whereby n is between 1.0 and 5.0; and/or
    iii) the reaction composition comprises $SiO_2$ originating from the silicate salt in a concentration that lies in a range from 0.01 to 0.75 mol/l.
12. The method according to claim 1, wherein the reaction composition is prepared by:
    providing core particles in an aqueous medium and agitating to form a suspension;
    adding the base in an amount to adjust the pH value to a pH value that lies above the gelation pH of silica;
    adding the silica salt; and
    adding the pH modulator after the core particles, the base and the silicate salt were added.
13. The method according to claim 1, comprising:
    a) providing an aqueous reaction composition comprising
       i) iron oxide containing core particles;
       ii) alkali hydroxide as base;
       iii) potassium silicate as silicate salt in a concentration of 0.01 to 0.75 mol/l; and
       iv) formamide as pH modulator,
    wherein the pH value of the reaction composition is 12.5 or above;
    b) stirring said reaction composition, wherein the pH modulator is hydrolysed at the pH value of the reaction composition thereby continuously decreasing the pH value of the reaction composition to a pH value in range of 9.5 to 11.5, wherein due to said decrease of the pH value of the reaction composition, $SiO_2$ is deposited onto the core particles, and wherein the $SiO_2$ coated core particles aggregate to provide discrete porous particles which have a diameter that lies in a range of 500 nm to 15 µm; and
    c) obtaining the porous particles.
14. The method according to claim 13, comprising:
    aa)
       preparing iron oxide core particles by adding one or more iron salts to an aqueous alkali hydroxide solution to precipitate magnetite or maghemite as core particles; and adding potassium hydroxide, potassium silicate and formamide to said core particles containing solution, thereby forming the reaction composition of step a); or bb) suspending iron oxide core particles in an aqueous solution; and adding potassium hydroxide, potassium silicate and formamide to said core particles containing suspension, thereby forming the reaction composition of step a).

15. The method according to claim 1, wherein the core particles are magnetite particles, the silicate salt is potassium silicate, the pH modulator is formamide, and the initial pH value of the reaction composition is adjusted to a pH value of 13 to 14 by using potassium hydroxide; and wherein the reaction composition is agitated at room temperature.

16. The method according to claim 1, wherein the obtained particles have a porous structure, have a size as determined based on the diameter of 20 μm or less, and are formed by agglomerated $SiO_2$ coated magnetic core particles.

17. The method according to claim 1, having one or more of the following characteristics:
i) in step b), the reaction composition is continuously stirred for at least 1 hour;
ii) the reaction composition is stirred between 12 and 20 hours;
iii) the coating that is deposited onto the core particles consists of $SiO_2$;
iv) the coating that is deposited onto the core particles comprises $SiO_2$ and one or more additional oxide compounds selected from $B_2O_3$, $Al_2O_3$, $TiO_2$, $ZrO_2$, $Na_2O$, $K_2O$, $CaO$ and $MgO$; and/or
v) the method comprises a step of functionalizing the surface of the obtained silica particles.

18. The method according to claim 1, wherein after the particle formation is completed, and optionally after an aging step, the particles are collected from the reaction composition either by sedimentation, filtration, decantation, centrifugation or by application of a magnetic field in case magnetic silica particles were produced.

19. A method for isolating nucleic acids, from a sample comprising:
a) binding the biomolecule contained in the sample to the silica-coated particles prepared by the method according to claim 1;
b) separating the particles with the bound biomolecule from unbound components;
c) optionally washing the bound biomolecule; and
d) optionally eluting the bound biomolecule.

20. Porous silica particles having a size of 30 μm or less and formed by agglomerated $SiO_2$ coated core particles, wherein the core particles are essentially encapsulated by the $SiO_2$ coating, wherein the silica particles have a composition regarding the comprised $SiO_2$ and core particles that is 15 to 75% (by weight) core particles and 25% to 85% (by weight) $SiO_2$, and wherein the silica particles are capable of binding at least 20 μg nucleic acid molecules per mg particles.

21. The silica particles according to claim 20, wherein the particles comprise macropores.

22. The silica particles according to claim 21, wherein the surface of the particles also comprises micropores.

23. The silica particles according to claim 20, wherein the particles have a size of 25 μm or less.

24. The silica particles according to claim 23, wherein the particles have a size of 10 μm or less.

25. The silica particles according to claim 23, wherein the particles have a size of 3 μm or less.

26. The silica particles according to claim 20, wherein the silica particles have a composition regarding the comprised $SiO_2$ and core particles that is 20 to 50% (by weight) core particles and about 50 to 80% (by weight) $SiO_2$.

27. The silica particles according to claim 26, wherein the silica particles have a composition regarding the comprised $SiO_2$ and core particles that is 25 to 50% (by weight) core particles and about 50 to 75% (by weight) $SiO_2$.

28. The silica particles according to claim 20, having one or more of the following characteristics:
i) the core particles have magnetic properties;
ii) the core particles have superparamagnetic, paramagnetic, ferromagnetic or ferrimagnetic properties;
iii) the core particles comprise iron oxide;
iv) the core particles have a diameter that lies in a range from 8 to 150 nm, and/or
v) the core particles are hollow.

29. The silica particles according to claim 28, wherein the core particles comprise magnetite or maghemite.

30. The silica particles according to claim 28, wherein the core particles have a diameter that lies in a range from 10 nm to 60 nm.

31. The silica particles according to claim 20, wherein the nucleic acid binding capacity of the particles is determined as described in example 6.

32. The silica particles according to claim 20, wherein the silica particles are obtainable by a method comprising:
a) providing an aqueous reaction composition comprising
i) core particles,
ii) an added base,
iii) a silicate salt, and
iv) a pH modulator
wherein the pH value of the reaction composition is above the gelation pH value of the silica salt;
b) agitating said reaction composition, wherein the pH modulator is an organic compound that reacts in the alkaline milieu of the reaction composition, thereby decreasing the pH value of the reaction composition over time and wherein due to said decrease of the pH value of the reaction composition, $SiO_2$ is deposited onto the core particles, whereby particles are formed which have a diameter of 30 μm or less; and
c) obtaining the particles.

33. A method for isolating nucleic acids, from a sample comprising:
a) binding the biomolecule contained in the sample to the silica-coated particles of claim 20;
b) separating the particles with the bound biomolecule from unbound components;
c) optionally washing the bound biomolecule; and
d) optionally eluting the bound biomolecule.

34. The silica particles according to claim 20, wherein the surface of the porous silica particles is functionalized with one or more chemical functionalities or ligands.

35. The silica particles according to claim 20, wherein the surface of the porous silica particles is not functionalized with a chemical functionality or ligand.

* * * * *